(12) United States Patent
Stupp

(10) Patent No.: US 8,639,446 B1
(45) Date of Patent: Jan. 28, 2014

(54) TECHNIQUE FOR IDENTIFYING ASSOCIATION VARIABLES

(75) Inventor: Steven Elliot Stupp, San Carlos, CA (US)

(73) Assignee: Trigeminal Solutions, Inc., San Carlos, CA (US)

( * ) Notice: Subject to any disclaimer, the term of this patent is extended or adjusted under 35 U.S.C. 154(b) by 736 days.

(21) Appl. No.: 12/456,561

(22) Filed: Jun. 18, 2009

Related U.S. Application Data

(60) Provisional application No. 61/132,946, filed on Jun. 24, 2008.

(51) Int. Cl.
*G06F 19/00* (2011.01)

(52) U.S. Cl.
USPC .......................................................... 702/19

(58) Field of Classification Search
None
See application file for complete search history.

(56) References Cited

U.S. PATENT DOCUMENTS

| | | | | |
|---|---|---|---|---|
| 2003/0009295 | A1* | 1/2003 | Markowitz et al. | 702/20 |
| 2004/0175700 | A1* | 9/2004 | Geesaman | 702/19 |

OTHER PUBLICATIONS

McLachlan et al. (Bioinformatics, vol. 22 No. 13, p. 1608-1615, 2006).*
Shmulevich et al. (PNAS, vol. 102, No. 38, p. 13439-13444, Sep. 20, 2005).*
Schaid et al. (Am. J. Hum. Genet., vol. 70, p. 425-434, 2002).*
Posterior probability. (2000). In Collins English Dictionary. Retrieved from http://www.credoreference.com/entry/hcengdict/posterior_probability.*
M.D. Ritchie et al., "Multifactor-dimensionality reduction reveals high-order interactions among estrogen-metabolism genes in sporadic breast cancer," Am J Hum Genet., vol. 69(1), pp. 138-147 (2001).
M.D. Ritchie et al., "Power of multifactor dimensionality reduction for detecting gene-gene interactions in the presence of genotyping error, missing data, phenocopy, and genetic heterogeneity," Genetic Epidemiology, vol. 24, pp. 150-157 (2003).
Yanging Chen et al., "Variations in DNA elucidate molecular networks that cause disease," Nature vol. 452/27, pp. 429-435, Mar. 2008.
Jonathan Marchini et al., "Genome-wide strategies for detecting multiple loci that influence complex diseases," Nature Genetics vol. 37/4, pp. 413-417, Apr. 2005.
Jonathan Marchini et al., "A new multipoint method for genome-wide association studies by imputation of genotypes," Nature Genetics, vol. 39, pp. 906-913, Jun. 2007.
Tong T. Wu, Yi F. Chen, Trevor Hastie, Eric Sobel and Kenneth Lange, "Genome-wide association analysis by Lasso penalized logistic regression," Bioinformatics, vol. 25(6), pp. 714-721, Mar. 2009.

* cited by examiner

*Primary Examiner* — Lori A Clow

(74) *Attorney, Agent, or Firm* — Steven Stupp

(57) ABSTRACT

An apparatus, and related method, for identifying one or more association variables that are associated with a trait are described. During the method, the apparatus may calculate statistical relationships corresponding to a pattern of occurrence of the trait in a group of life forms and patterns of occurrence of compound variables in a set of biological variables of the group of life forms. Then, the apparatus may determine a ranking of a number of occurrences of biological variables in at least a subset of the compound variables that have statistical relationships greater than a statistical confidence value. Next, the apparatus may identify one or more of the biological variables in the set of biological variables as the one or more association variables based on the ranking.

20 Claims, 11 Drawing Sheets

SEQUENCE LISTING

```
<160> NUMBER OF SEQ ID NOS: 2

<210> SEQ ID NO 1
<211> LENGTH: 11
<212> TYPE: DNA
<213> ORGANISM: Homo Sapiens

<400> SEQUENCE: 1
aacctaccac   a                                                      11

<210> SEQ ID NO 2
<211> LENGTH: 11
<212> TYPE: DNA
<213> ORGANISM: Homo Sapiens

<400> SEQUENCE: 2
aacttaccac   a                                                      11
```

TECHNIQUE FOR IDENTIFYING ASSOCIATION VARIABLES

CROSS REFERENCE TO RELATED APPLICATIONS

This application claims the benefit under 35 U.S.C. 119(e) to U.S. Provisional Application Ser. No. 61/132,946, entitled "Technique for identifying association variables," by inventor Steven E. Stupp, filed on Jun. 24, 2008, the contents of which are herein incorporated by reference.

SEQUENCE LISTING

The sequence listing for this application has been submitted in accordance with 37 CFR 1.52(e) and 37 CFR 1.821 on a CD-R in lieu of paper on a disk containing the sequence listing file entitled "SEQLIST.txt," created Oct. 21, 2011, which includes 373 bytes. Applicants hereby incorporate by reference the sequence listing provided on a CD-R in lieu of paper into the instant specification.

FIELD OF THE INVENTION

The present invention relates generally to an apparatus, and related methods, for processing data, and more specifically, for identifying association variables, such as biological variables, which are associated with a trait.

BACKGROUND

Many mathematical problems involve analyzing data to determine relationships between variables. For example, in regression analysis an expression can be determined to describe data (which is sometimes referred to as 'fitting' the expression to the data). This is shown in FIG. 1A, which presents a graph 100 illustrating the fitting a line to data. The equation for a line y (the independent variable) can be expressed as $$y=mx+b,$$

where x (the data) is the dependent variable, and m and b are unknown coefficients (the slope and y-intercept, respectively) that are to be determined during the fitting. In this example, each datum in the data corresponds to a point in the x-y plane (such as $x_0$, $y_0$).

Typically, the minimum number of data points needed to uniquely determine the fitting equation equals the number of unknown in the fitting equation (as shown in FIG. 1A, for a line, the minimum number of data points is two). If there are more data points than this minimum number, statistical techniques such as least-squares regression may be used to determine the unknown coefficients. However, if there are fewer data points available than the minimum number, it is typically not possible to uniquely determine the unknowns. This is shown in FIG. 1B, which presents a graph 150 illustrating the fitting of multiple lines to a datum. In principle, there are an infinite number of equivalent fitting solutions that can be determined. This type of problem is sometimes referred to as underdetermined.

Unfortunately, many interesting problems are underdetermined. For example, in biology, important differences between different individual's genomes are described by single nucleotide polymorphisms (SNPs). As shown in FIG. 2, which presents a graph 200 illustrating a SNP 210, a SNP is a deoxyribonucleic-acid (DNA) sequence variation that occurs when a single nucleotide, such as adenine (A), thymine (T), cytosine (C), or guanine (G), in a chromatid in the genome (or another shared sequence) differs between members of a species (or between paired chromosomes in an individual). For example, two sequenced DNA fragments from different individuals, AACCTACCACA (SEQ ID NO: 1) to AACCTACCACA (SEQ ID NO: 2), contain a difference in a single nucleotide (in this case, there are two alleles, C and T). Variations in the DNA sequences of humans can affect how humans develop diseases and respond to pathogens, chemicals, drugs, vaccines, and other agents. Consequently, there is great interest in identifying associations between SNPs and the expression of such traits or phenotype information in a population of individuals, such as matched cohorts with and without a disease.

However, even after eliminating correlated SNPs using a haplotype map (which includes information about closely related alleles that are inherited as a unit), there may still be several hundred thousand or more SNPs for each individual in a population. In order to identify the associations, these SNPs may be compared to the expression of a trait in the population, such as the occurrence of a disease. Typically, the population may include several hundred individuals. Consequently, identifying the associations involves 'fitting' several hundred thousand SNPs (the fitting space) to several hundred data points, which is an extremely underdetermined problem that increases the complexity, time and expense when trying to identify the associations.

Furthermore, it is unusual for a disease (or, more generally, an expressed trait) to be associated with a single gene. More typically, the disease is associated with multiple genes (i.e., it is polygenetic), as well as one or more environmental factors. In the case of SNPs, including these additional variables and/or combinations of variables causes a power-law increase in the size of the fitting space. If the population size (several hundred people) remains unchanged, the problem becomes vastly underdetermined. Unfortunately, increasing the size of the population is often difficult because of the associated expense and time needed to obtain biological samples.

Therefore, there is a need for an analysis technique to identify associations in underdetermined problems without the problems listed above.

SUMMARY OF THE INVENTION

One embodiment of the present invention describes an apparatus to identify one or more association variables that are associated with a trait. This apparatus may include at least one processor, at least one memory, and at least one program module. The program module may be stored in the memory and may be configurable and/or configured to be executed by the processor. The program module may include instructions for calculating statistical relationships corresponding to a pattern of occurrence of the trait in a group of life forms and patterns of occurrence of compound variables in a set of biological variables of the group of life forms. Note that a given statistical relationship corresponds to the pattern of occurrence of the trait in the group of life forms and a pattern of occurrence of a given compound variable in the set of biological variables of the group of life forms. Moreover, the pattern of occurrence of the given compound variable corresponds at least to a pattern of occurrence of a first biological variable in the set of biological variables of the group of life forms, and the calculating includes contributions from presence and absence information in the patterns of occurrence of the compound variables. Additionally, the program module may include instructions for determining a ranking of a number of occurrences of biological variables in at least a subset of the compound variables that have statistical relationships greater than a statistical confidence value, and may include instructions for identifying one or more of the biological variables in the set of biological variables as the one or more association variables based on the ranking.

In some embodiments, the given compound variable corresponds to at least to the pattern of occurrence of the first biological variable in the set of biological variables of the group of life forms and a pattern of occurrence of a second biological variable in the set of biological variables of the group of life forms. Moreover, the given compound variable may be determined by performing a logical operation on corresponding entries in the pattern of occurrence of the first biological variable and the pattern of occurrence of the second biological variable. This logical operation may include AND, OR, NOT, XOR and/or another Boolean operation.

In some embodiments, the statistical confidence value corresponds to a statistical significance value associated with the statistical relationships. Moreover, the statistical confidence value may correspond to a noise floor in the statistical relationships. This noise floor may be determined based on a stability of at least a portion of the ranking for statistical confidence values between the statistical confidence value and another statistical confidence value, which is larger than the statistical confidence value.

In some embodiments, the program module includes instructions for determining the set of biological variables of the group of life forms based on biological samples associated with the group of life forms.

In some embodiments, the program module includes instructions for subtracting another ranking from the ranking prior to identifying the one or more association variables, where the other ranking corresponds to a number of occurrences of the biological variables in another subset of the compound variables that have additional statistical relationships greater than another statistical confidence value. These additional statistical relationships may correspond to a sequence of values and the patterns of occurrence of the compound variables in the set of biological variables of the group of life forms. Moreover, a given additional statistical relationship may correspond to the sequence of values and the pattern of occurrence of the given compound variable in the set of biological variables of the group of life forms.

Note that the other statistical confidence value may be different than the statistical confidence value. For example, the sequence of values may include a random or a pseudorandom sequence of values. Moreover, a number of entries in the sequence of values may equal a number of life forms in the group of life forms.

In some embodiments, the set of biological variables include categorical data. Alternatively and/or additionally, the program module may include instructions for converting the set of biological variables into categorical data.

In some embodiments, the set of biological variables includes information associated with single nucleotide polymorphisms (SNPs). Moreover, the program module may include instructions for converting the set of biological variables into binary categorical data. Note that the converting for a given genetic locus (such as a base-pair location) may be based on a minor allele frequency (or a major allele frequency) of a SNP at the given genetic locus.

In some embodiments, a given pattern of occurrence of a given variable, which can include the trait in the group of life forms, the given compound variable, or the first biological variable, includes presence and absence information of the given variable associated with the group of life forms. Note that the presence information of the given variable may include expression or suppression of the given variable and/or the absence information of the given variable may include an absence of expression or an absence of suppression of the given variable.

In some embodiments, the set of biological variables include environmental factors.

In some embodiments, the program module includes instructions for excluding at least some of the compound variables prior to calculating the statistical relationships, where a given excluded compound variable may have a number of presences or absences in its pattern of occurrence that is greater than a first value or less than a second value. Alternatively or additionally, the program module may include instructions for excluding at least some of the biological variables in the set of biological variables prior to calculating the compound variables, where a given excluded biological variable has a number of presences or absences in its pattern of occurrence that is greater than a third value or less than a fourth value.

In some embodiments, the calculating involves a non-parametric statistical analysis technique, such as: a chi-square analysis technique, a log-likelihood ratio analysis technique, a goodness-of-fit (G-test) technique, and/or a Fisher's exact probability analysis technique.

Moreover, the calculating may involve a supervised learning technique. This supervised learning technique may include a support vector machines (SVM) analysis technique and/or a classification and regression tree (CART) analysis technique.

In some embodiments, the trait includes phenotype information and/or a disease. This disease may include: a type of cancer, an auto-immune disease, an immune-related disease, a form of arthritis, a disease of at least a portion of the endocrine system, a metabolic disease, cardiovascular disease, a neurological disease, a respiratory disease, joint disease, gastrointestinal disease, a disease of a component in blood, a psychological disease, asthma, an allergy, an inflammatory disease, a disease involving a histamine response, a chronic disease, and/or an episodic disease.

In some embodiments, biological variables in the set of biological variables include epi-genetic information, information associated with deoxyribonucleic acid, information associated with ribonucleic acid, information associated with one or more proteins, and/or information associated with another biological marker.

In some embodiments, the life forms include: humans, animals, and/or plants.

In some embodiments, the apparatus includes a computer system.

In some embodiments, a number of life forms in the group of life forms is significantly less than a number of biological variables in the set of biological variables.

Another embodiment provides a first circuit to identify the one or more association variables that are associated with the trait. This circuit includes a statistical computation circuit to calculate the statistical relationships. Moreover, the circuit includes a ranking circuit to determine the ranking of the number of occurrences of the biological variables in at least the subset of the compound variables, and an analysis circuit to identify the one or more of the biological variables in the set of biological variables as the one or more association variables based on the ranking.

Another embodiment provides a second circuit to identify the one or more association variables that are associated with the trait, where the second circuit is configured and/or configurable to perform operations corresponding to at least some of the instructions in the program module.

Another embodiment provides a method for identifying the one or more association variables that are associated with the trait. This method may include other operations corresponding to at least some of the instructions in the program module.

Another embodiment provides a computer-program product for use in conjunction with the apparatus.

The disclosed embodiments facilitate the identification of associations in underdetermined problems and/or provide an analysis technique to identify the one or more association variables that are associated with the trait.

BRIEF DESCRIPTION OF THE DRAWINGS

Note that like reference numerals refer to corresponding parts throughout the drawings.

DETAILED DESCRIPTION

Figure 1A:
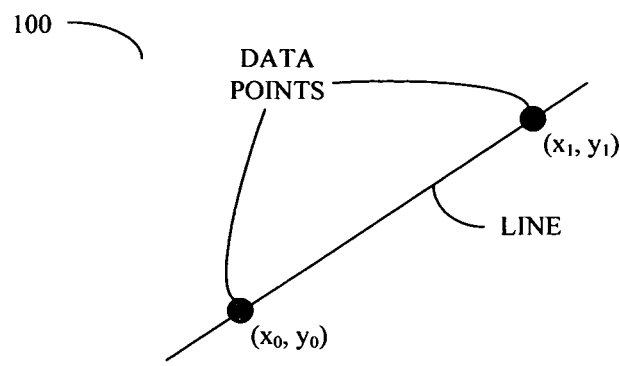
FIG. 1A is a graph illustrating fitting a line to data.
Figure 1B:
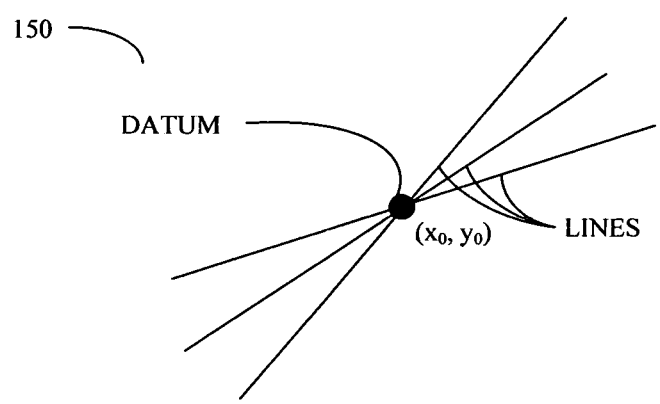
FIG. 1B is a graph illustrating fitting multiple lines to a datum.

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the claims.

Embodiments of an apparatus (such as a computer system or a circuit), a method, and a computer-program product (e.g., software) for use with the apparatus are described. This apparatus may be used to identify one or more association variables that are associated with a trait. In particular, compound variables may be determined for biological variables in a set of biological variables of a group of life forms (such as genetic data for a group of people, animals, and/or plants). (Alternatively, the compound variables may be pre-determined.) A given compound variable may be determined using one or more biological variables, where a given entry in the compound variable for a given one of the life forms is based on a presence or absence of the one or more biological variables for the given one of the life forms. For example, the given entry may be determined by performing a logical operation (AND, OR, NOT, XOR and/or another Boolean operation) on the values of one or more biological variables of the given life form. Alternatively, the given entry in the compound variable for the given one of the life forms is based on an expression or suppression of one or more biological variables for the given one of the life forms.

Then, the apparatus may calculate statistical relationships between a pattern of occurrence of the trait associated with a group of life forms (e.g., presence or absence of the trait in the group of life forms) with patterns of occurrence of compound variables in a set of biological variables of the group of life forms (e.g., presence or absence entries in the compound variables). These calculations may involve a non-parametric statistical analysis technique and/or a supervised learning technique.

Next, the apparatus may determine a ranking a number of occurrences of biological variables in a subset of the compound variables that have statistical relationships greater than a statistical significance value, which may correspond to a noise floor in the statistical relationships. This noise floor may be determined based on a stability of at least a portion of the ranking for statistical confidence values between the statistical confidence value and another statistical confidence value, i.e., a range of statistical confidence values.

Moreover, the apparatus may identify one or more of the biological variables as the one or more association variables based on the ranking (for example, N association variables may be the top-N values in the ranking).

In some embodiments, the apparatus performs a correction for a background prior to identifying the one or more association variables. For example, the apparatus may subtract another ranking which is associated with a number of occurrences of the biological variables in other statistically significant statistical relationships (i.e., those compound variables which have statistical relationship values greater than another statistical significance value) between the pattern of occurrence of the compound variable and a sequence of values (such as a random or a pseudo-random sequence of values).

In the discussion that follows, the following definitions are used:

- the meaning of 'configured' may include 'to set up for operation especially in a particular way', such as a circuit configured for a particular function or a program configured to be executed on a particular processor or computer;
- the meaning of 'configurable' may include 'capable of being configured in a particular way', such as a programmable circuit that is configurable or a program (source code or compiled) that can be configured to executed on the particular processor at run time;
- the meaning of 'based on' may include 'is a function of', 'using' and/or 'according to';

the meaning of 'group of life forms' may include 'a group that includes one or more people, animals, and/or plants';

the meaning of 'pattern of occurrence of a variable or a trait for a group of life forms' may include 'values corresponding to presence or absence information for the variable or the trait for each of the life forms in the group', 'values corresponding to expression or non-expression information for the variable or the trait for each of the life forms in the group', 'values corresponding to suppression or non-suppression information for the variable or the trait for each of the life forms in the group', and/or 'values corresponding to expression or suppression information for the variable or the trait for each of the life forms in the group'(note that non-expression or non-suppression may be equivalent and may correspond to a value between expression and suppression);

the meaning of 'ranking' may include 'a listing of items in a group according to a system of rating';

the meaning of 'allele' may include two or more alternative forms of a genetic locus, where a single allele for each genetic locus is inherited separately from each parent (e.g., at a genetic locus for eye color an allele might result in blue or brown eyes);

the meaning of 'phenotype' may include 'the observable traits or characteristics of an organism, such as hair color, weight, or the presence or absence of a disease, which may not be genetic or may not be solely genetic';

the meaning of 'epi-genetic' may include 'something that affects a cell, organ, plant, animal or individual (i.e., a human) without directly affecting its DNA, which may indirectly influence the expression of the genome'; and the meaning of 'disease' may include 'an illness or sickness characterized by an impairment of health or a condition of abnormal functioning'.

In general, the trait includes phenotype information, such as: how life forms (for example, humans) develop diseases and respond to pathogens, chemicals, drugs (or pharmacological agents), vaccines, and/or other agents. In some embodiments, the trait includes a disease. This disease may include: a type of cancer, an auto-immune disease, an immune-related disease, a form of arthritis, a disease of at least a portion of the endocrine system, a metabolic disease, cardiovascular disease, a neurological disease, a respiratory disease, joint disease, gastrointestinal disease, a disease of a component in blood, a psychological disease, asthma, an allergy, an inflammatory disease, a disease involving a histamine response, a chronic disease, and/or an episodic disease. For example, the disease may include: rheumatoid arthritis, lupus, thyroid disease, gout, diabetes, chronic fatigue syndrome, insomnia, depression, anxiety, bipolar disorder, colitis, ulcerative colitis, inflammatory bowel disease, Crohn's disease, candida, celiac disease, irritable bowel syndrome, one or more food allergies, one or more food sensitivities, menstrual cramps, chronic pain, back pain, facial pain, fibromyalgia, asthma, migraines, abdominal migraines, cyclic vomiting syndrome, cluster headaches, chronic headaches, tension headaches, another type of headaches, seizures, epilepsy, neurodermatitis, acne, psoriasis, adiposity, hypertonia, heart disease, hypertension, arteriosclerosis, and/or acquired immune deficiency syndrome. In some embodiments, the trait may include multiple illnesses, which may or may not have an associated comorbidity.

We now describe embodiments of a technique for identifying one or more association variables that are associated with a trait. In the discussion that follows, SNPs are used as an illustration of biological variables. However, in other embodiments the biological variables may include: epi-genetic information (such as methylation or demethylation), information associated with DNA (such as one or more copy number variations or frame shifts), information associated with ribonucleic acid (RNA), information associated with one or more proteins (such as one or more enzymes), and/or information associated with another biological marker or type of biological marker.

Note that in some embodiments the biological variables include environmental factors, such as: environmental stimuli (for example, light or sound), weather conditions, behaviors, patterns of behaviors (when the behaviors occur or do not occur), diet (including foods or beverages consumed or not consumed), dietary patterns (when the foods or beverages are consumed or are not consumed), use of drugs (prescription or recreational), activities, exposure to chemicals, exposure to toxins, exposure to one or more fungi, and/or exposure to infectious agents (for example, bacteria, viruses, and/or prions).

Figure 2:
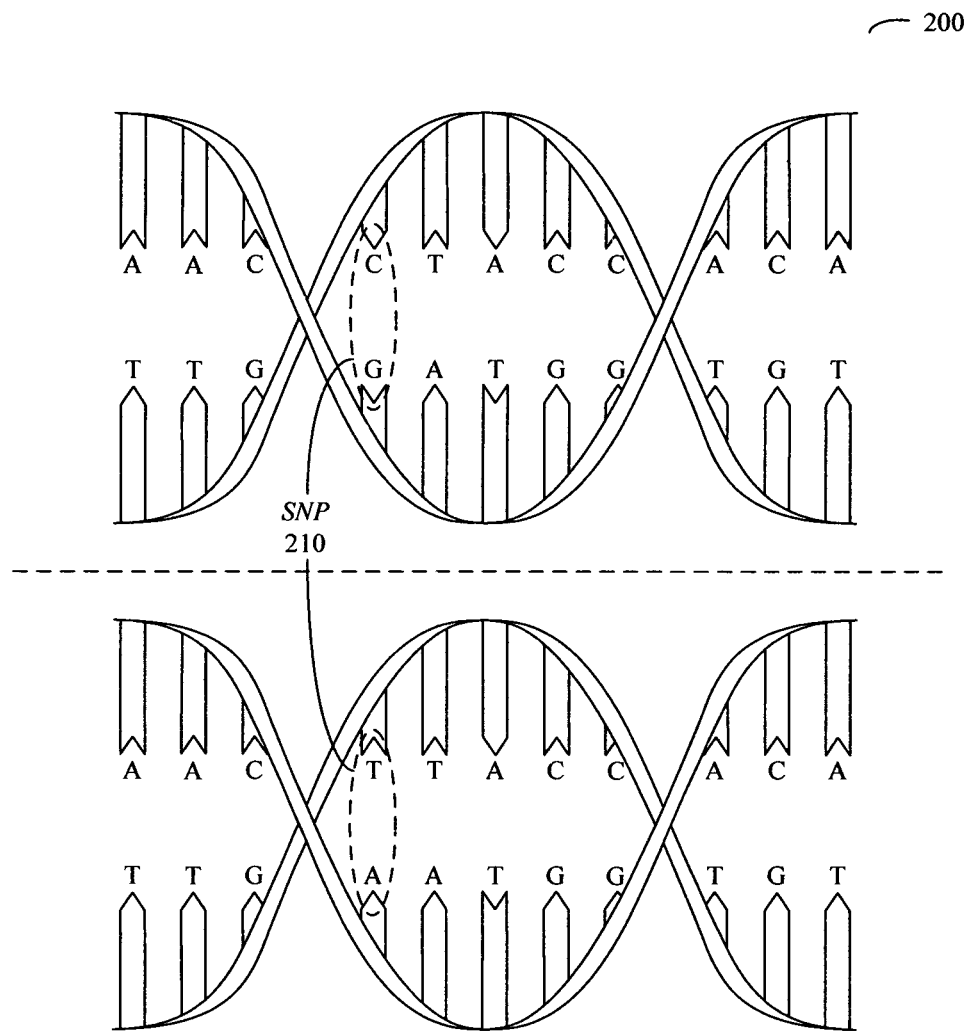
FIG. 2 is a drawing illustrating a single nucleotide polymorphism (SNP) at a single base-pair location, where AACCTACCACA is SEQ ID NO: 1 and AACTTACCACA is SEQ ID NO: 2.

Continuing the discussion of FIG. 2, SNPs may fall within coding sequences of genes, non-coding regions of genes, or in the intergenic regions between genes. Because of the degeneracy of the genetic code, SNPs within a coding sequence may not necessarily change the amino acid sequence of the protein that is produced. A SNP in which both forms lead to the same polypeptide sequence is termed 'synonymous' (sometimes called a silent mutation). However, if a different polypeptide sequence is produced they are 'non-synonymous'. Note that SNPs that are not in protein-coding regions may still have consequences for gene splicing, transcription factor binding, or the sequence of non-coding RNA.

Most common SNPs have only two alleles. It is important to note that there are variations between populations (such as between groups of humans), so a SNP allele that is common in one geographical or ethnic group (such as a given population or a given group of life forms) may be much rarer in another. Typically, in order for a variation to be considered a SNP, it occurs in at least 1% of a given population.

SNPs can be assigned a minor allele frequency, which is the lowest allele frequency at a genetic locus (such as a base-pair location) that is observed in a particular or given population. This is simply the lesser of the two allele frequencies for SNPs. Similarly, SNPs can be assigned a major allele frequency, which is the largest allele frequency at the genetic locus (such as the base-pair location) that is observed in the given population. This is simply the larger of the two allele frequencies for SNPs.

Figure 3:
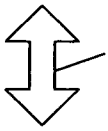
FIG. 3 is a drawing illustrating converting biological variables into categorical data in accordance with an embodiment of the present invention, where AACCTACCACA is SEQ ID NO: 1.

For the given population, the minor allele frequencies and/or the major allele frequencies may be used to convert a sequence of SNPs at multiple genetic loci to categorical or discrete data. In an exemplary embodiment, the categorical data includes two classes or categories, i.e., binary categorical data. This is shown in FIG. 3, which presents a drawing 300 illustrating converting biological variables in SEQ ID NO: 1 into categorical data. In particular, SNP information is converted during conversion 314 into binary data. For example, at base-par locations, such as base-pair location 310, SNPs having a minor allele frequency may be coded as '0's. Similarly, at the other base-par locations, SNPs having a major allele frequency may be coded as '1's.

More generally, categorical data may be represented by codes. For categorical variables having two class or categories, a single binary digit may be used, such as 0 or 1, or −1 or 1. Thus, in the case of SNPs, genetic loci corresponding to minor frequencies may be coded as −1s and genetic loci corresponding to major frequencies may be coded as 1s. Note that a wide variety of code choices may be used.

Also note that, when there are more than two categories, such as A, T, C, and G for a DNA sequence, a dummy variable having K values or bits may be used. Moreover, data having qualitative or continuous values can be converted in to categorical data by partitioning using one or more thresholds. In some embodiments, different thresholds may be used for different biological variables or different types of biological variables (such as SNPs versus environmental factors). Furthermore, in some embodiments categorical data is converted into continuous values using interpolation (such as minimum bandwidth interpolation), subject to the limitations associated with the Nyquist sampling criterion.

In some embodiments, either before conversion to binary categorical data or after, SNP data for a given population may be windowed or reduced using a haplotype map for the given population. This windowing operation may remove SNPs at genetic loci in the data that are highly correlated with one or more other SNPs in the data. For example, many SNPs are highly correlated with each other over or across one or more regions in the genomes or sequences of most or all of the given population. For each group of highly correlated SNPs in the data, all but one may be removed from the set of biological variables associated with the given population before attempting to identify the one or more association variables.

Figure 4A:
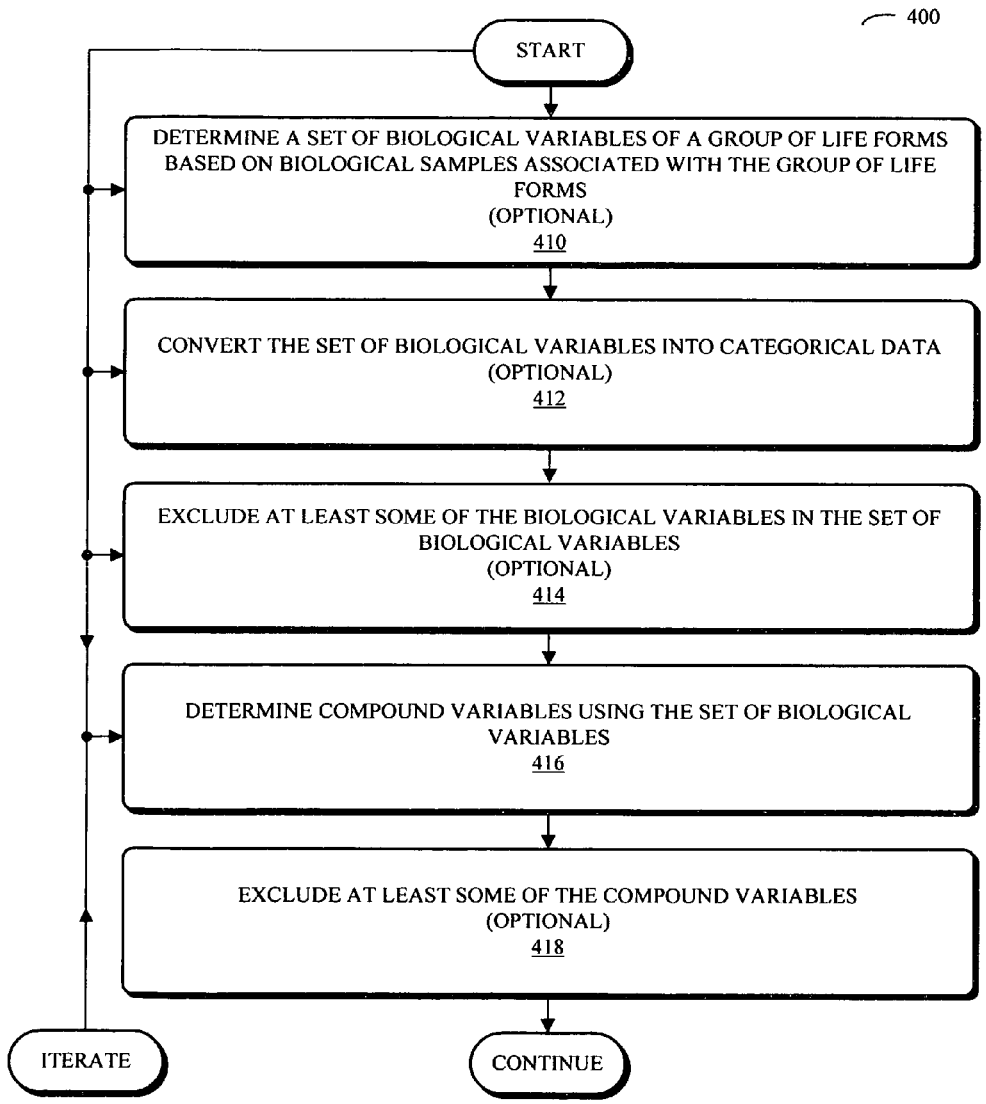
FIG. 4A is a flow chart illustrating a process for identifying one or more association variables that are associated with a trait in accordance with an embodiment of the present invention.

FIG. 4A presents a flow chart illustrating a process 400 for identifying one or more association variables that are associated with a trait. During this process, a set of biological variables of the group of life forms is optionally determined based on biological samples associated with the group of life forms (410). For example, biological variables may be determined by analyzing one or more biological samples for each member of the group of life forms, thereby determining the set of biological variables. These biological samples may include: a blood sample, a urine sample, a stool sample, a saliva sample, a sweat sample, a mucus sample, a skin scrapping, and/or a tear. Moreover, the analysis may include chemical analysis, genetic analysis (such as genetic sequencing), nuclear quadrapole resonance, nuclear magnetic resonance, and/or electron spin resonance.

Then, the set of biological variables may be optionally converted into categorical data (412), as described previously in the discussion of FIG. 3.

Next, at least some of the biological variables in the set of biological variables may be optionally excluded (414) prior to determining compound variables using the set of biological variables (416) (or a remainder of the set of biological variables after the optional excluding 414). For example, a given excluded biological variable may have a number of presence or absences (or, alternatively, expression and/or suppression) in a pattern of occurrence in the set of biological variables (i.e., in the data determined from the biological samples of the group of life forms) which is greater than a first value or less than a second value. This may exclude biological variables that have too few or too many presences or absences for there to be a statistically significant relationship with a pattern of occurrence of the trait associated with the group of life forms. For these excluded biological variables, it may not be possible to determine whether or not there is a relationship with the trait. In an exemplary embodiment, the first value is 85% presence or absence (respectively) and/or the second value is 15% absence or presence (respectively).

Additionally, or alternatively, in some embodiments at least some of the determined compound variables may be optionally excluded (418) after determining the compound variables (416). For example, a given excluded compound variable may have a number of presence or absences (or, alternatively, expression and/or suppression) in a pattern of occurrence of the compound variable (i.e., based on the data associated with the group of life forms) which is greater than a third value or less than a fourth value. This may exclude compound variables that have too few or too many presences or absences for there to be a statistically significant relationship with a pattern of occurrence of the trait associated with the group of life forms. For these excluded compound variables, it may not be possible to determine whether or not there is a relationship with the trait. In an exemplary embodiment, the third value is 85% presence or absence (respectively) and/or the fourth value is 15% absence or presence (respectively).

As noted above, the compound variables may be determined (416). (Alternatively, the compound variables may be pre-determined, stored in a computer-readable memory, and accessed during process 400.) Moreover, as described further below, this determining or accessing may be iterated 426 (FIG. 4B) at increasingly higher orders, which facilitates the identification of the one or more association variables using hierarchical feature extraction. For example, at first order, a given compound variable may correspond to a pattern of occurrence of a given biological variable.

Then, at second order, a given compound variable may correspond to a pattern of occurrence of one biological variable in the set of biological variables of the group of life forms and a pattern of occurrence of a another biological variable in the set of biological variables of the group of life forms. This process may be repeated at ever high order (i.e., with larger groups of biological variables) until the resulting model complexity is sufficient to 'fit' the data or until diminishing returns occur (as described further below).

Note that the given compound variable for an order n may be determined by performing an operation and/or a logical operation on corresponding entries in the patterns of occurrence of n biological variables. For example, at second order, a particular compound variable may be determined by performing the operation and/or the logical operation on corresponding entries in a pattern of occurrence of a first biological variable and a pattern of occurrence of the second biological variable (which is described further below with reference to FIG. 5). This operation may include multiplication. Moreover, the logical operation may include a Boolean operation, such as AND. However, a wide variety of coding approaches may be used in different embodiments for representing presence and absence information in the patterns of occurrence of biological variables. Therefore, in some embodiments the logical operation may include AND, OR, NOT, XOR, and/or another Boolean operation.

In some embodiments, one or more compound variables may be a weighted summation of one or more biological variables. For example, for order n, n biological variables may be multiplied by corresponding weights and summed to determine the given compound variable. Moreover, in some embodiments the resulting one or more compound variables may be converted into categorical data using one or more thresholds (thus, converting operation 412 may occur before and/or after the determining operation 416).

Figure 4B:
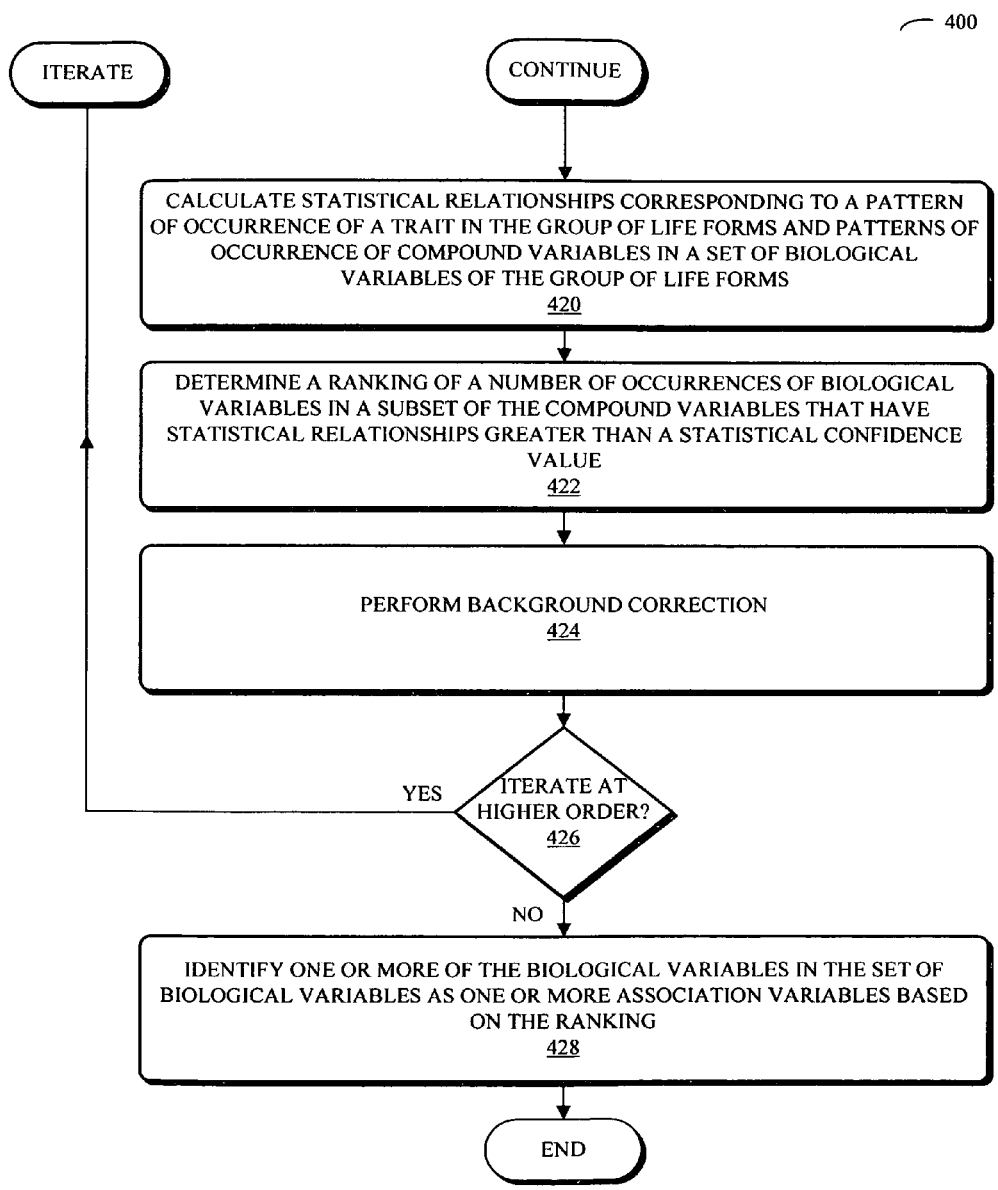
FIG. 4B is a flow chart illustrating a process for identifying one or more association variables that are associated with a trait in accordance with an embodiment of the present invention.

Continuing the discussion of process 400 in FIG. 4B, then statistical relationships corresponding to a pattern of occurrence of the trait in a group of life forms and patterns of occurrence of compound variables in a set of biological variables of the group of life forms may be calculated (420). In particular, a given statistical relationship may correspond to the pattern of occurrence of the trait in the group of life forms and the pattern of occurrence of the given compound variable in the set of biological variables of the group of life forms. Note that the calculation may include contributions from presence and absence information (or, alternatively, expression and/or suppression information) in the patterns of occurrence of the compound variables and/or in the patterns of occurrence of the trait.

As described further below, the statistical relationships may be determined using a supervised-learning analysis technique and/or a non-parametric analysis technique, which makes few assumptions about an existence of a probability distribution function, such as a normal distribution, corresponding to the given population from which biological samples and, thus, the data are obtained, or regarding independence of: the biological variables and/or the compound variables. In some embodiments, a given statistical relationship may be used to perform hypothesis testing to determine if the associated compound variable and the trait are statistically independent (or dependent) based on a statistical confidence value (for example, based on a statistical significance value or criterion). In the process, the effective signal-to-noise ratio in an underdetermined problem (e.g., sparse sampling in a multi-dimensional variable space, such as when a number of life forms in the group of life forms is significantly less than a number of biological variables in the set of biological variables) may be improved by restricting a number of local fitting neighborhoods (e.g., a number of relevant biological variables and/or compound variables), thereby reducing the requirements associated with the Bonferonni correction.

Note that in some embodiments 'significantly less than' includes a multiplicative factor of 2, 5, 10, 100, 1000, $10^4$, $10^5$, $10^6$, $10^7$, or more. Thus, the number of life forms in the group of life forms may be 1000 times less than the number of biological variables in the set of biological variables. In an exemplary embodiment, there number of life forms is 500 and the number of biological variables in the set of biological variables is 500,000.

Next, a ranking of a number of occurrences of biological variables in a subset of the compound variables that have statistical relationships greater than a statistical confidence value may be determined (422). (This is described further below with reference to FIG. 6.)

Moreover, a background correction may be performed (424). For example, the additional statistical relationships may be calculated (420) using a sequence of values (such as a random or a pseudorandom sequence having the same number of entries as the number of life forms in the group of life forms) instead of the pattern of occurrence of the trait. Then, another ranking for another subset of these additional statistical relationships that are significant may be determined (422) and may be subtracted from the ranking. Note that significance of the other subset of the additional statistical relationships may be determined using another statistical confidence value, which may be different that the statistical confidence value.

As noted previously, operations 416-424 may be iterated (426) using progressively higher-order compound variables to determine the statistical relationships and the ranking. In some embodiments, at least a portion of the ranking for the current order is used to determine the compound variables (416) (FIG. 4A) at the next higher order. As described further below, these iterations may be continued until a model that describes the relationship between the patterns of occurrence of the compound variables in the set of biological variables and the pattern of occurrence of the trait is obtained or diminishing returns occur (such as an increase in an error associated with predictions of the model based on training data and test data).

Next, one or more of the biological variables in the set of biological variables may be identified (428) as the one or more association variables based on the ranking. As described further below with reference to FIG. 7, the one or more association variables may be identified in rankings that are above a noise floor in the statistically significant compound variables. For example, at least a subset of such rankings may be stable, and the biological variables in such subsets may be the one or more association variables. As is also described further below, note that the one or more association variables may have a relationship or an anti-relationship with the occurrence of the trait in the given population.

In some embodiments, process 400 includes additional or fewer operations. Moreover, the order of the operations may be changed and/or two or more operations may be combined into a single operation. For example, in some embodiments compound variables may be determined (416) (FIG. 4A) using biological variables associated with time intervals (which may be the same as each other, may be different than each other, and/or may be offset from each other) that precede a change in the trait in individual life forms in the group of life forms (such as the occurrence of cancer, an increase of a symptom, and/or an onset of an episode of an episodic disease). In some embodiments, the time intervals include: minutes, hours, days, months, and/or years. In an exemplary embodiment for migraines, at second order, a particular compound variable corresponds to a pattern of occurrence of a first biological variable in a first time interval preceding one or more migraines (such as one day before each migraine in a sequence of migraines) and a pattern of occurrence of a second biological variable in a second time interval preceding the one or more migraines (such as between one and two days before each migraine in the sequence of migraines).

In some embodiments, at least some of the operations in process 400 (FIGS. 4A and 4B) are repeated to identify subgroups or subpopulations in the given population or group of life forms. For example, one or more subgroups may be determined based on the one or more identified association variables for different portions of the group of life forms. Note that the one or more subgroups may be indicative of underlying polymorphism in a genetic basis for a given trait.

Figure 5:
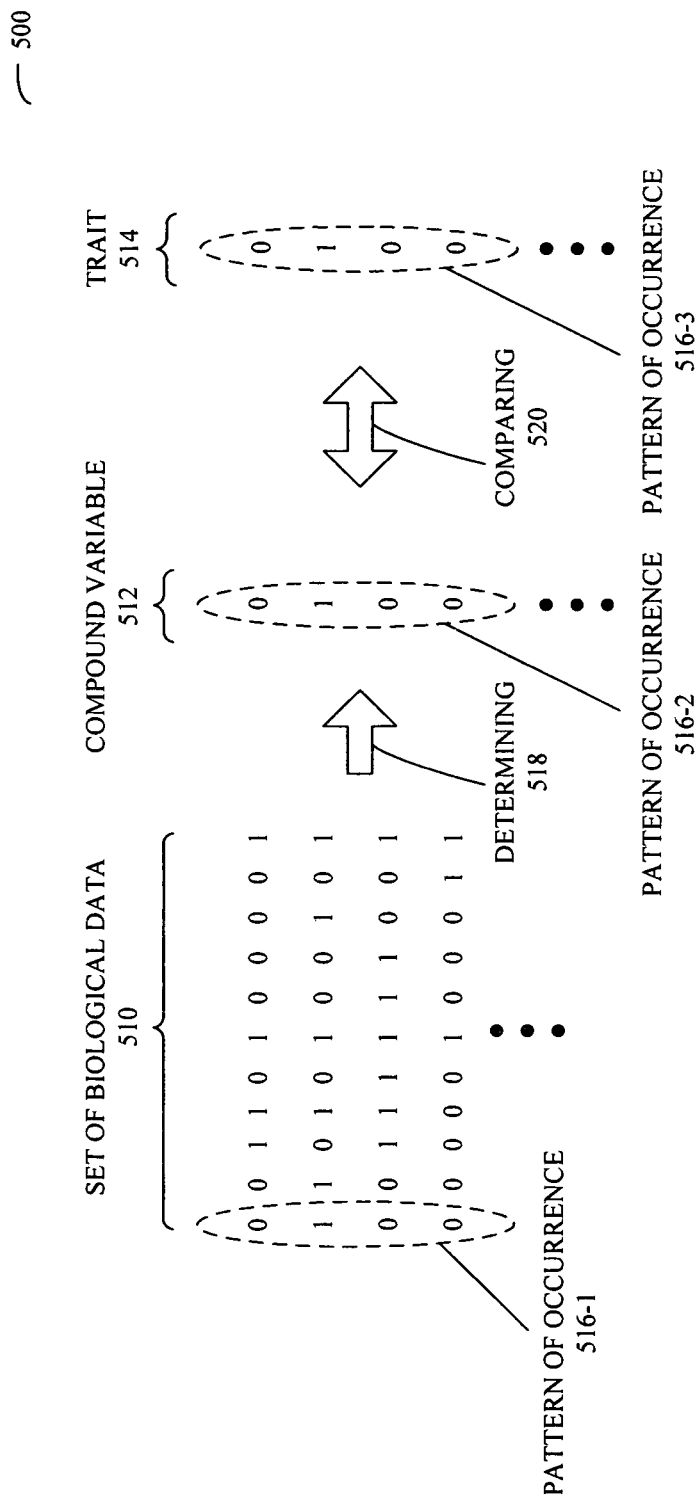
FIG. 5 is a drawing illustrating identifying one or more association variables that are associated with a trait in accordance with an embodiment of the present invention.

We now describe examples of operations in process 400 (FIGS. 4A and 4B). FIG. 5 presents a drawing 500 illustrating identifying one or more association variables that are associated with a trait. Set of biological variables 510 may include multiple biological variables (the columns) associated with multiple life forms in a group of life forms (the rows). In general, the presence or absence (or, expression and/or suppression) of a given biological variable varies in the data and, thus, across or over the group of life forms. (For example, for a given life form, presence of the given biological variable may be indicated by a '1' and absence of the given biological variable may be indicated by a '0'.) This variation defines the patterns of occurrence of each of the biological variables, such as pattern of occurrence 516-1.

Similarly, information for the occurrence of trait 514 may vary across or over the group of life forms (the rows in trait 514). For example, trait 514 may be present in one life form (as indicated by a '1') and absent in another (as indicated by a '0'). (Alternatively, '0's and '1's may indicate suppression and expression, respectively, of trait 514.) This variation defines the patterns of occurrence 516-3 of trait 514.

Moreover, one or more biological variables in the set of biological variables 510 may be used to determine 518 compound variable 512. For example, at second order, row entries in the first two columns in the set of biological variables 510 may be logically ANDed, such that two '1' row entries for a given life form in the group of life forms results in a '1' row entry in compound variable 512, etc. In general, the resulting entries in compound variable 512 may vary across or over the group of life forms (the rows in compound variable 512). This variation defines the patterns of occurrence 516-2 of compound variable 512.

Then, patterns of occurrence 516-2 and 516-3 may be used to calculate a statistical relationship for each life form in the group of life forms (i.e., using the entries in compound variable 512 and trait 514 on a row by row basis). For example, the statistical relationship may be determined by comparing 520 entries in compound variable 512 and trait 514 using a statistical analysis technique. This process may be repeated for multiple combinations of the biological variables (i.e., multiple compound variables) in the set of biological variables 510 to generate a set of statistical relationships with trait 514 for a given order in the analysis.

Figure 6:
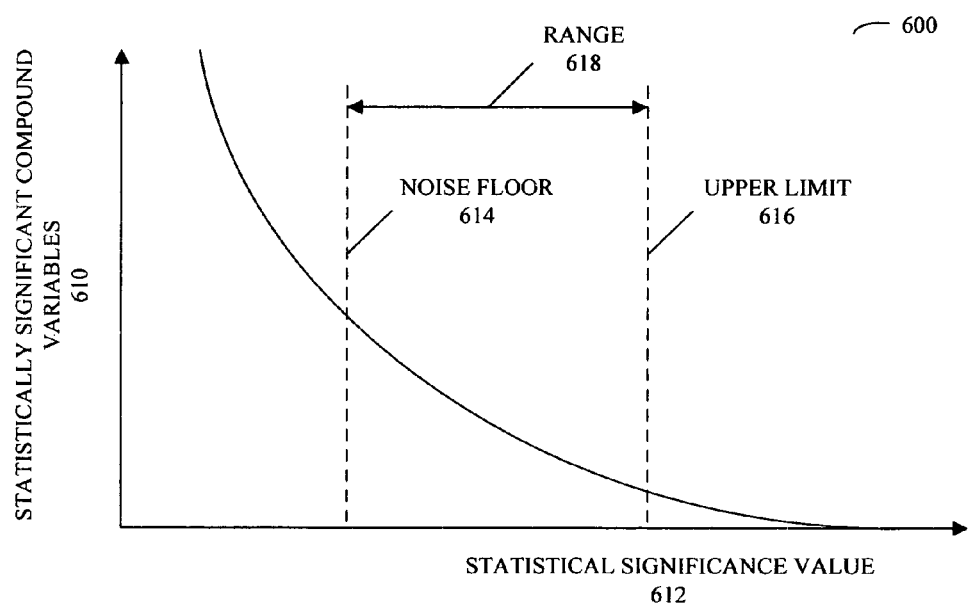
FIG. 6 is a graph of statistically significant compound vectors as a function of statistical significance value in accordance with an embodiment of the present invention.

Next, the set of statistical relationships may be compared to statistical confidence values (such as a statistical significance value or criterion) to identify a noise floor in the set of statistical relationships. This is shown in FIG. 6, which presents a graph 600 of statistically significant compound vectors 610 (i.e., compound vectors having statistical relationships with the trait that exceed a statistical significance value) as a function of statistical significance value 612. As the statistical significance value 612 is increased, the number of statistically significant compound vectors 610 decreases. If the signal-to-noise ratio in the set of biological variables 510 (FIG. 5) and the trait 514 (FIG. 5) is sufficiently large (for a given size of or number of members in the group of life forms) then at least a portion of rankings of the number of occurrences of biological variables in the statistically significant compound vectors 610 between a minimum value of the statistical significance value 612 and an upper value 616 of the statistical significance value 612 is substantially or approximately stable. (One metric for whether or not the signal-to-noise ratio is sufficiently large is if the expectation value for the number of statistically significant compound variables for a given statistical significance value is less than the actual number of statistically significant compound vectors at the given statistical significance value.) This minimum value is the noise floor 614. Note the upper value 616 occurs because, eventually, as the statistical significance value 612 is increased, the number of statistically significant compound vectors 610 decreases to the point where the remaining statistically significant compound vectors 610, and thus the corresponding rankings, are dominated by statistical outliers. Consequently, for a large enough statistical significance value 612, the ranking may no longer be substantially or approximately stable.

Figure 7:
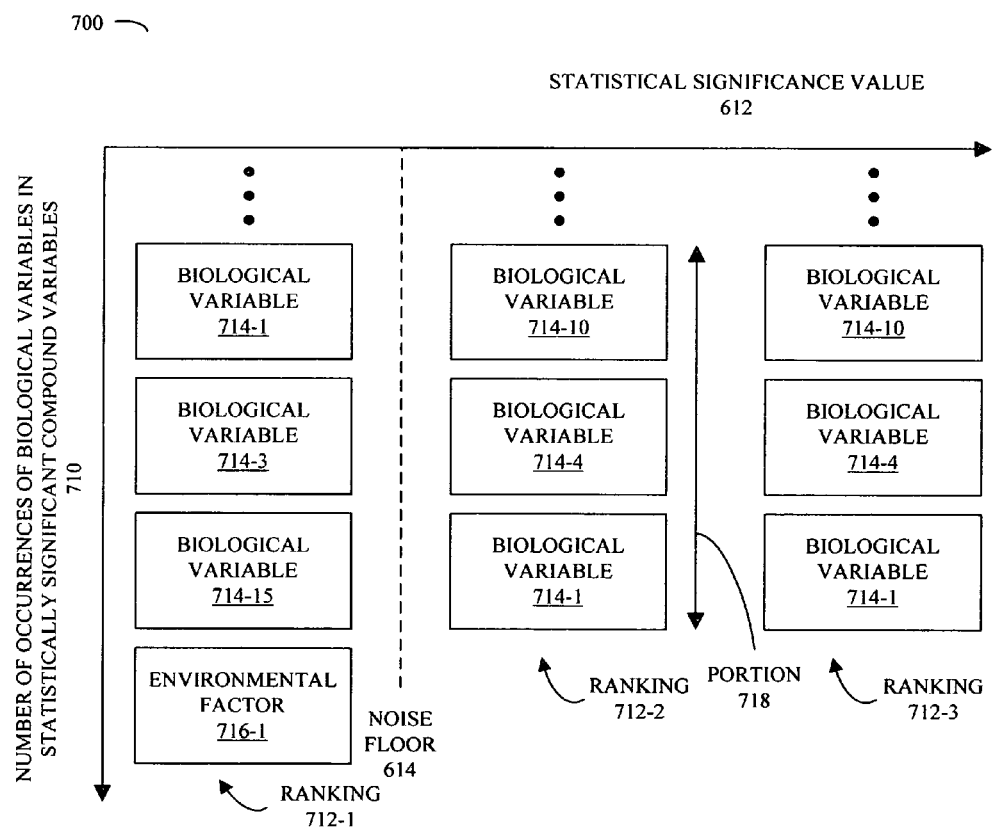
FIG. 7 is a graph of a ranking of a number of occurrences of biological variables in statistically significant relationships as a function of statistical significance value in accordance with an embodiment of the present invention.

FIG. 7 is a graph 700 of a ranking of a number of occurrences of biological variables in statistically significant compound variables 710 as a function of statistical significance value 612. As the statistical significance value 612 increases, at least a portion 718 of rankings, such as rankings 712-2 and 712-3, above the noise floor 614 is substantially or approximately stable. (In contrast, ranking 712-1 may not be stable, i.e., when the statistical significance value 612 increases, ranking 712-1 may change.) For example, a given ranking, such as ranking 712-2, may be considered to be substantially or approximately stable if 50%, 70%, 75%, 80%, 85%, 90%, 95% or 100% of the top-N biological variables (such as the top-10) in the given ranking are unchanged when the statistical significance value 612 is increased.

Note that portion 718 may include one or more biological variables, such as environmental factor 716-1 and/or one or more of biological variables 714. Moreover, at least portion 718 in rankings 712-2 and 712-2 may indicate a pareto. Furthermore, the one or more association variables may be identified in portion 718 or in rankings 712-2 and 712-3 that are substantially or approximately stable.

We now further describe embodiments of the statistical analysis. This statistical analysis may include classification and/or regression (such as determining a model of the one or more traits, which includes one or more biological variables and/or one or more compound variables, along with corresponding weights).

A wide variety of computational techniques may be used to determine the one or more statistical relationships, including: one or more parametric analysis techniques, one or more non-parametric analysis techniques, one or more supervised learning techniques and/or one or more unsupervised learning techniques. In some embodiments, one or more non-parametric analysis techniques may be used. As noted previously, non-parametric analysis techniques make few assumptions about an existence of a probability distribution function, such as a normal distribution, corresponding to the given population (or group of life forms) from which samples or associated data are obtained, or regarding independence of the biological variables and/or the compound variables. In general, non-parametric analysis techniques may use rank or naturally occurring frequency information in the data to draw conclusions about the differences between different populations or subsets of the given population.

Note that the one or more non-parametric analysis techniques may perform hypothesis testing, e.g., to test a statistical significance of a hypothesis. In particular, the one or more non-parametric analysis techniques may determine if the one or more traits and/or the one or more compound variables are statistically independent (or dependent) based on a statistical significance value or criterion. As noted previously, one or more compound variables having a statistically significant relationship with the trait (and, in particular, the pattern of occurrence of the trait for the group of life forms) may be used to identify the one or more association variables.

In exemplary embodiments, the non-parametric analysis technique may include: a chi-square analysis technique, a log-likelihood ratio analysis technique (also referred to as G-test), and/or a Fisher's exact probability analysis technique. In addition to their other advantages, these techniques may be well suited to analyzing an underdetermined problem, i.e., sparse sampling in a multi-dimensional variable space, in which there may be multiple biological variables and/or compound variables and a smaller number of members of the group of life forms (and thus, a smaller number of entries in these variables and in the trait information).

In some embodiments, the chi-square analysis technique, the log-likelihood ratio analysis technique, and/or the Fisher's exact probability analysis technique may be determined using a cross-tabulation or contingency tables (which are sometimes referred to as bivariate tables). Note that the Fisher's exact probability analysis technique computes the sum of conditional probabilities of obtaining the observed frequencies in a given contingency table and the conditional probabilities of obtaining exactly the same observed frequencies for any configuration that is more extreme, i.e., having a smaller conditional probability. Moreover, the chi-square ($\chi^2$) may be determined using $$\chi^2 = \sum_i \frac{(O_i - E_i)^2}{E_i},$$

and the log-likelihood ratio (LLR) using $$LLR = \sum_i O_i \ln\left(\frac{O_i}{E_i}\right),$$

where the summation is over the entries in the given contingency table, $O_i$ is the i-th observed frequency value, and $E_i$ is the i-th expected frequency value. The following example illustrates an embodiment of determining a statistical relationship using the log-likelihood ratio for binary categorical data.

Consider the example in Table I. The first column contains the number of entries in the pattern of occurrence where a compound variable is present and the trait is present (which is henceforth denoted by $X_{11}$) in the data (such as genetic data) associated with the group of life forms plus the number of entries in the pattern or occurrence where the compound variable is absent and the trait is absent in the data associated with the group of life forms (which is henceforth denoted by $X_{00}$). $X_{11}$ is sometimes referred to as a true-true and $X_{00}$ is sometimes referred to as a false-false. $X_1$, and $X_{00}$ are henceforth referred to as co-occurrences.

(Note that there are, in principle, three additional related contingency tables for which statistical relationships can be determined, in which true-true is based on: (1) the number of occurrences when the compound variable is present and the trait is absent plus the number of occurrences when the compound variable is absent and the trait is present, (2) the number of occurrences when the compound variable is absent and the trait is present plus the number of occurrences when the compound variable is present and the trait is absent, and (3) the number of occurrences when the compound variable is absent and the trait is absent plus the number of occurrences when the compound variable is present and the trait is present, respectively.)

The second column in Table I contains the number of entries in the pattern of occurrence where the compound variable is present and the trait is absent (henceforth denoted by $X_{10}$) in the data associated with the group of life forms plus the number of entries in the pattern of occurrence where the compound variable is absent and the trait is present (henceforth denoted by $X_{01}$) in the data associated with the group of life forms. $X_{10}$ is sometimes referred to as a true-false and $X_{01}$ is sometimes referred to as a false-true. $X_{10}$ and $X_{01}$ are henceforth referred to as cross occurrences.

Table I. An example of a contingency table.

TABLE I

An example of a contingency table.

| Number of Co-Occurrences ($X_{11} + X_{00}$) | Number of Cross Occurrences ($X_{10} + X_{01}$) |
|---|---|
| 46 | 11 |

If the compound variable and the trait are completely independent, the expected frequency values for each column, $E_1$ and $E_2$, would equal 28.5, one half of the sum of the number of co-occurrences and cross occurrences, i.e., the total number of observations (data points or samples) in Table I. Therefore, for Table I, $$LLR = 2 \cdot 46\ln\left(\frac{46}{28.5}\right) + 2 \cdot 11\ln\left(\frac{11}{28.5}\right) = 44.04 - 20.94 = 23.10.$$

A one-sided minimal statistical significance confidence value or criterion of 5% ($\alpha=0.05$) or a statistical confidence threshold based on the number of degrees of freedom (the size of the contingency table, which in this example is one) corresponds to an LLR of 3.841. (Note that if the biological variables have more than two categories, the contingency table may have a larger number of degrees of freedom.) Because the LLR for Table I is greater than 3.841, it is statistically significant. Therefore, from a statistical perspective, the patterns of occurrence of the compound variable and the trait in the data associated with the group of life forms in this example are dependent.

Note that it is possible for statistically significant LLR values to occur even when $X_{11}$ is zero. In some embodiments, compound variables that have $X_{11}$ equal to zero when compared with the pattern of occurrence of the trait are excluded prior to determining the ranking and identifying the one or more association variables. Additionally, note that the LRR value is the same when there is a relationship (when the number of co-occurrences is greater than the number of cross occurrences) or an anti-relationship (when the number of co-occurrences is less than the number of cross occurrences) between the pattern of occurrence of the compound variable and the pattern of occurrence of the trait. Consequently, in embodiments where association variables corresponding to relationships are desired, statistical relationships where the number of co-occurrences is less than the number of cross occurrences may be excluded. Similarly, in embodiments where association variables corresponding to anti-relationships are desired, statistical relationships where the number of co-occurrences is greater than the number of cross occurrences may be excluded. Furthermore, in some embodiments, instead of using a ranking corresponding to the sequence of values to perform the background correction, a ranking of the number of occurrences of biological variables in statistical relationships corresponding to no relationship (i.e., an LLR of infinity, or when the number of co-occurrences equals the number of cross occurrences) may be used.

In the preceding example, the calculation of the statistical relationship for the trait and the compound variable uses presence and absence information in the patterns of occurrence of the compound variable and the trait. In some embodiments, one or more of the statistical relationships may be determined using presence information, i.e., the presence only (or absence only) of one or more compound variables in the data associated with the group of life forms, without using absence information (or without using presence information). In alternate embodiments, a wide variety of analysis techniques may be used to calculate the one or more statistical relationships.

In parametric analysis, a Pearson's product-moment correlation coefficient r may be useful in summarizing a statistical relationship. For some contingency tables, Cramer's phi $\phi$, the square root $\chi^2$ of or the LLR divided by the number of observations N, may have a similar interpretation to r (although, it is known that Cramer's phi may underestimate r). In the example illustrated in Table I, $$\varphi = \sqrt{\frac{LLR}{N}} = \sqrt{\frac{23.1}{57}} = 0.64.$$

The chi-square analysis technique and the log-likelihood ratio analysis technique may have a maximal sensitivity for contingency tables based on patterns of occurrence of compound variables having 50% presence entries and 50% absence entries in the data associated with the group of life forms. In addition, maximal sensitivity may occur if 50% of the life forms in the group of life forms have the trait, e.g., presence entries. In some embodiments, one or more contingency tables may be generated to achieve approximately 50% presence entries for patterns of occurrence of one or more compound variables and/or 50% having the trait by using a subset of the data associated with the group of life forms. In an exemplary embodiment, one or more contingency tables may be generated by randomly or pseudo-randomly selecting (for example, using a pseudo-random number generator or algorithm) a subset of the data associated with the group of life forms, such that the one or more contingency tables may have approximately 50% presence entries and 50% absence entries distributed over $X_{00}$, $X_{11}$, $X_{10}$, and $X_{01}$. For infrequently occurring events, biological variables and/or compound variables, there may be more absence entries than presence entries in the data associated with the group of life forms. As a consequence, different sampling ratios may be used for presence and absence entries in the data associated with the group of life forms.

In some embodiments, boosting may be used when generating one or more contingency tables. A subset of the data associated with group of life forms may be selected randomly or pseudo-randomly in order to determine one or more contingency tables. A given contingency table may be generated L times using approximate random sampling. Statistical relationships for at least M of these L contingency tables may be used (including combining and/or averaging) to determine whether or not the trait and the corresponding compound variable are independent in the data associated with the group of life forms. In an exemplary embodiment, L may be 5, 10, 25, 50, 100, 500 or more, and M may be 50% (rounded to the nearest integer), 60%, 66%, 70%, 75%, 80% or more of L.

In some embodiments, there may be too few presence entries or too many presence entries in one or more patterns of occurrence of one or more biological variables or compound variables in the data associated with the group of life forms to reliably determine statistically significant independence (or dependence) based on the trait information for the group of life forms, i.e., the pattern of occurrence of the trait in data associated with the group of life forms. As a consequence, one or more of these biological variables or one or more of these compound variables may be excluded when determining one or more statistical relationships. In an exemplary embodiment, one or more variables or one or more compound variables having patterns of occurrence with less than 15% presence entries or more than 85% presence entries in the data associated with the group of life forms may be excluded.

Overfitting or developing a model that is too complex is a risk in a statistical learning problem. In some embodiments, the model complexity may correspond to a number of compound variables that have statistically significant dependence on the trait information. Moreover, in some embodiments the model complexity may, at least in part, correspond to a number of biological variables included when determining a given compound variable, i.e., the order n.

In some embodiments, this risk may be addressed using a fraction or percentage of the data associated with the group of life forms (such as the patterns of occurrence) for training, i.e., to develop the model, and a remainder for testing the resulting model. Typically training error decreases as the model complexity increases (the model better fits or predicts a training set of data), and a testing error exhibits a minimum. Additional model complexity beyond this minimum usually does not generalize well (the model offers a poorer fit or prediction for a test set of data). Therefore, beyond the minimum point the training set of data may be overfit. In an exemplary embodiment, the percentage of the data associated with the group of life forms used for training may be 70%, 75%, 80%, 85% or 90%.

An additional metric of the model complexity may be determined. This metric may be used in conjunction with or independently of the training set of data and the test set of data. The additional metric is described below. In some problems and/or embodiments, calculating one or more statistical relationships for one or more biological variables (or, said differently, for one or more compound variables of order 1) may not be sufficient to determine statistically significant independence (or dependence) with respect to trait information. For example, in multi-dimensional problems, where two or more biological variables are necessary and sufficient to give rise to a trait (such as migraine), a value of the Fisher's exact probability, $\chi^2$, and/or LLR for a compound variable of order 1 may be reduced since there is a penalty for the presence of the cross occurrences, $X_{10}$ and $X_{01}$.

More generally, the value of the Fisher's exact probability, $\chi^2$, and/or LLR may be reduced if the order n of one or more compound variables is less than an intrinsic order of the multi-dimensional problem. In the case of $X_{10}$, a trait may or may not occur unless a certain number of biological variables or a set of biological variables (which may be inter-operative) are present for particular life forms in the group of life forms. And in the case of $X_{01}$, more than one set of biological variables may be present, i.e., one or more biological variables in another set of biological variables may lead to the trait in the particular life forms. (Moreover, for environmental factors, there may be one or more thresholds, which may be a function of time.)

To assess whether or not the model has sufficient complexity, i.e., whether or not one or more compound variables have been determined to sufficient order n, a ratio R may be determined. For contingency Table I, R is defined as $X_{11}$ divided by the total number of occurrences of the compound variable of order n in the data associated with the group of life forms, i.e., $$R = \frac{X_{11}}{(X_{11} + X_{10})}.$$

An increasing value of R, and/or Cramer's phi $\phi$, as statistical analysis is performed to higher order (i.e., n+1) may be metrics of goodness, i.e., it may indicate that the higher order does a better job determining statistically significant independence or dependence between one or more compound variables and the trait information. In some embodiments, contingency tables for one or more compound variables may be generated for progressively higher orders (e.g., by iterating at least some of the operations in process 400 in FIGS. 4A and 4B). Once the ratio R is close to or equal to one, i.e., $X_{10}$ is close to or equal to zero, further increases in the order n of one or more compound variables may not be needed (the model has sufficient complexity). Note that in some embodiments, statistical entropy may be used to determine if further increases in the order n of one or more compound variables are needed.

One or more variables and/or compound variables having statistically significant statistical relationships with the trait information for the group of life forms may be identified as one or more association variables. For a given compound variable of order n having a significant statistical relationship with the trait information, the n constituent biological variables may be identified as n association variables and/or as a set of association variables. In some embodiments, one or more statistically significant compound variables of order n having the ratio R approximately equal to 1 may be identified as one or more association variables.

In some embodiments, one or more compound variables of order n and/or one or more constituent biological variables in the one or more compound variables of order n may be ranked based on the corresponding calculated statistical relationships that are statistically significant. In some embodiments, a ranking of a given constituent biological variable is based on a number of occurrences of the given constituent biological variable in one or more compound variables of order n having statistical relationships that are statistically significant. As noted previously, ranking may be performed as the statistical significance confidence value or criterion (α) is progressively increased, which can be used to determine the noise floor in the statistical relationships (as described previously in the discussion of FIG. 6, and as described further below).

In exemplary embodiments, cc may be 0.05 or lower. For a given ranking, a pareto corresponding to at least a portion of the given ranking may be defined. This pareto may correspond to biological variables or compound variables having a statistical relationship or a number of occurrences in the statistically significant compound variables exceeding a threshold. In some embodiments, a top-10, 20, 50 or 100 biological variables or compound variables may be used, or a majority of the top-10, 20, 50 or 100 biological variables or compound variables may be used. For compound variables of order n, approximate stability of the pareto as the statistical significance value or criterion is increased may be used to identify the noise floor. Approximately stability may include an approximately unchanged order of the ranking or a presence of approximately the same biological variables and/or compound variables (for example, more than 70%) in the portion of the ranking. In exemplary embodiments, the noise floor may correspond to an α of 0.01 or lower, an α of 0.001 or lower, or an α of 0.0001 or lower. One or more biological variables and/or one or more compound variables in paretos corresponding to one or more statistical significance values or criteria that exceed the noise floor may be identified as association variables.

In some embodiments, the analysis is repeated using a random or pseudo-random sequence of values instead of the trait information. This sequence of values may have the same length (or number of entries) as the number of life forms in the group of life forms. Moreover, the resulting ranking, which may be determined using the same or a different statistical significance value or criterion as the ranking described above, may be subtracted from the ranking described above before the one or more association variables are identified.

In some embodiments, one or more biological variables and/or one or more compound variables in paretos corresponding to one or more statistical significance values or criteria that exceed the noise floor may be used as a seed set in additional statistical analysis. The additional statistical analysis may determine statistical relationships for compound variables of a higher order. In some embodiments, the additional analysis may utilize an analysis technique such as SVM or CART.

Alternatively, the additional analysis technique may be used as the initial or first stage, to refine the model (including adding or removing one or more biological variables and/or one or more compound variables), and/or to identify one or more association variables.

Note that the additional analysis technique may include classification and/or regression (such as determining a model of the trait information including one or more biological variables and/or one or more compound variables, along with corresponding weights). As with the statistical analysis technique described previously, a wide variety of techniques may be used in the additional analysis technique. Two such techniques, SVM and CART, are described further below.

Embodiments of SVM are instances of supervised learning techniques that may be applied to classification and regression problems. For binary classification, a set of binary labeled data points (training data or examples) is provided. SVMs may be used to determine an optimal separation boundary, defined by the biological variables and/or compound variables, between two classes of data points. A separation boundary is optimal if using it as a decision rule to classify future data points minimizes an expected classification error. For linearly separable data sets (e.g., a class of absences, which may be indicated by −1, and a class of presences, which may be indicated by +1, that may be separated from each other by a line in 2 dimensions, or a so-called hyperplane in higher dimensions), SVMs may be used to determine a maximal margin hyperplane. For the maximal margin hyperplane, a linear decision boundary may be positioned such that it separates both classes and such that the distance to the closest point from each class is maximized. For non-linearly separable data sets, some training data points may be allowed on the opposite or 'wrong' side of the hyperplane, e.g., a classification error on the training data set may be allowed and may be minimized, while the margin, measured between points on the 'correct' side of the hyperplane, may be maximized.

If a linear decision boundary is not sufficiently complicated to model the separation between classes accurately, the corresponding linear model may be transformed into a non-linear model by non-linearly transforming the biological variables and/or compound variables into a possibly higher dimensional Euclidean space. A linear decision boundary constructed in such a higher dimensional Euclidean space may correspond to a non-linear decision boundary in the original space of biological variables and/or compound variables. This approach is referred to as kernel SVM.

Depending on how the margin and training error are measured, and how a trade-off between maximizing the margin and minimizing the training error is established, different types of SVMs may be obtained. In some embodiments, SVM may include standard 1-norm SVM (measuring the margin using Euclidean distance, i.e., a $L_2$-norm, and the training error using a $L_1$-norm), standard 2-norm SVM (measuring the margin using Euclidean distance, i.e., the $L_2$-norm, and the training error using the $L_1$-norm), and/or LP-SVM (measuring the margin using the $L_1$-norm and the training error using the $L_1$-norm). Each of these 3 types of SVM may be a C-type or η-type SVM. These two varieties correspond to different ways of trading-off maximizing the margin against minimizing the training error. The 1-norm SVM, standard 2-norm SVM, and/or LP-SVM may be a C+/C− or η+/η− type, where errors on positive (+1) labeled training data are weighted differently than errors on negative (−1) labeled training data.

The principle for binary classification described above may be extended to regression, for example, by copying the regression data twice, shifting both copies in opposite directions (over a distance epsilon) with respect to the continuous output dimension or variable and establishing a regression surface as a decision boundary between the two shifted copies that may be regarded as two classes for binary classification. As a consequence, in some embodiments, regression versions of SVMs corresponding to previously described SVMs may be used.

The decision boundary determined using one or more SVMs may be used to discriminate between presence and absence of the trait in the trait information associated with the group of life forms. For binary classification, measures of goodness for the resulting model include a prediction accuracy that is better than predicting 50% of the positive data (e.g., occurrences, which may be indicated by a +1) as positive (i.e., true positive predictions) and better than predicting 50% of the negative data (i.e., absences, which may be indicated by a −1) as negative (i.e., true negative predictions). Doing better than 50/50 corresponds to doing better than random.

CART is a non-parametric multivariate analysis technique. It involves the determination of a binary decision tree using the training set of data. Predictions based on the resulting tree may be compared to the test set of data (cross validation). A decision tree provides a hierarchical representation of the feature space in which explanatory variables are allocated to classes (such as presence or absence of the trait in the trait information) according to the result obtained by following decisions made at a sequence of nodes at which branches of the tree diverge. Branches or divisions of the tree may be chosen to provide the greatest reduction in the statistical entropy of the variables (for a classification tree based on categorical data), such as a small or zero standard deviation, or the greatest reduction in the deviation between the biological variables (and/or compound variables) and the trait being fit (for a regression tree based on quantitative data). A tree stops growing when no significant additional reduction can be obtained by division. A node that is not further sub-divided is a terminal node. It is associated with a class. A desirable decision tree is one having a relatively small number of branches, a relatively small number of intermediate nodes from which these branches diverge, terminal nodes with a non-zero number of entries, and high prediction power (correct classifications at the terminal nodes). In some embodiments, CART may be used in conjunction with a gradient boosting algorithm, where each boosted tree is combined with its mates using a weighted voting scheme. Gradient boosting may be used to force the binary decision tree to classify data that was previously misclassified.

As noted above, a wide variety of statistical analysis techniques may be used to determine the one or more statistical relationships. These may include: one or more supervised learning techniques, one or more unsupervised learning techniques, one or more parametric analysis techniques (such as a Pearson's product-moment correlation coefficient r or an inner product), and/or one or more non-parametric analysis techniques. Non-parametric analysis techniques may include: a Wilcoxon matched pairs signed-rank test (for ordinal or ranked data), a Kolmogorov-Smirnov one-sample test (for ordinal or ranked data), a dependent t-test (for interval or ratio data), a Pearson chi-square, a chi-square test with a continuity correction (such as Yate's chi-square), a Mantel Heanszel chi-square test, a linear-by-linear association test, a maximum likelihood test, a risk ratio, an odds ratio, a log odds ratio, a Yule Q, a Yule Y, a phi-square, a Kappa measure of agreement, a McNemar change test, a Mann Whitney U-test, a Spearman's rank order correlation coefficient, a Kendall's rank correlation, a Krushcal-Wallis One-Way Analysis of Variance, and/or a Turkey's quick test.

Supervised learning techniques may include: least-squares regression (including correlation), ridge regression, partial least-squares (also referred to as partial correlation), a perceptron algorithm, a Winnow algorithm, linear discriminant analysis (LDA), Fisher discriminant analysis (FDA), logistic regression (LR), a Parzen windows classifier, a (k-) nearest-neighbor classification, multivariate adaptive regression splines (MARS), multiple additive regression trees (MART), SVM, LASSO (a regularized linear regression technique like ridge regression, but with $L_1$-norm regularization of the coefficients), least angle regression (LARS), decision trees (such as CART, with and without gradient boosting, such as ID3 and C4.5), bagging, boosting (such as, adaboost) of simple classifiers, kernel density classification, a minimax probability machine (MPM), multi-class classification, multi-label classification, a Gaussian Process classification and regression, Bayesian statistical analysis, a Naive Bayes classifier, and/or neural networks for regression and classification. While some of these supervised learning algorithms are linear, it should be understood that one or more additional non-linear versions may be derived using the same 'kernel-methodology', as previously described for the SVM, leading to a spectrum of kernel-based learning methods, for example, kernel FDA, kernelized logistic regression, the kernelized perceptron algorithm, etc. One or more of these non-linear versions may be used to perform the statistical analysis.

Unsupervised learning techniques may include: a kernel density estimation (using, for example, Parzen windows or k-nearest neighbors), more general density estimation techniques, quantile estimation, clustering, spectral clustering, k-means clustering, Gaussian mixture models, an algorithm using hierarchical clustering, dimensionality reduction, principal component analysis (PCA), multi-dimensional scaling (MDS), isomap, local linear embedding (LLE), self-organizing maps (SOM), novelty detection (which is also referred to as single-class classification, such as single-class SVM or single-class MPM), canonical correlation analysis (CCA), independent component analysis (ICA), factor analysis, and/or non-parametric Bayesian techniques like Dirichlet processes. As noted above for the supervised learning techniques, one or more additional non-linear versions of one or more linear unsupervised learning techniques may be used to perform the statistical analysis, such as kernel. PCA, kernel CCA and/or kernel ICA.

In some embodiments, at least a portion of the statistical analysis, such as determination of one or more statistical relationships and/or identification of one or more association variables includes spectral analysis. For example, a Fourier transform or a discrete Fourier transform may be performed on the trait information, one or more patterns of occurrence of one or more biological variables, and/or one or more patterns of occurrence of one or more compound variables. Analysis in the frequency domain may allow patterns in at least some of the data associated with the group of life forms to be determined.

In some embodiments, calculating one or more statistical relationships and/or identifying one or more association variables includes the use of design of experiments. For example, the data associated with the group of life forms may correspond to an orthogonal array.

In some embodiments, a signal-to-noise metric is used to adjust how the one or more association variables are identified. This signal-to-noise metric may be computed using the set of biological variables of the group of life forms. Based on the computed signal-to-noise metric, how the one or more association variables are identified may vary from only using the ranking (for low values of the signal-to-noise metric) to only using the largest values of statistical association (i.e., without determining the ranking), which may be appropriate for high values of the signal-to-noise metric. In general, for an arbitrary value of the signal-to-noise metric, the one or more association variables may be identified using a weighted combination of the ranking and the largest values of statistical association, where the weights $\lambda i$ of these terms are a function of the signal-to-noise metric (for example, the weights of the two terms may be $\lambda$ and $1-\lambda$). Alternatively or additionally, such as weighted combination may be used in a modified version of a supervised learning technique, such as LASSO.

In some embodiments, the initial set of biological variables is pruned or reduced prior to identifying the one or more association variables based on known or pre-determined association variables for the trait, such as one or more genes associated with a disease that have been identified using: linkage analysis, the biochemistry of the disease, or another technique known to one of skill in the art.

We now describe embodiments of a circuit and a computer system that may perform at least a portion of the statistical analysis and/or the identifying of the one or more association variables. This circuit may contain one or more filters, including: analog filters, digital filters, adaptive filters (using, for example, a least-square error or gradient approach, such as steepest decent), and/or neural networks. The one or more filters may be implemented using one or more digital signal processors (DSPs). In some embodiments, the statistical analysis and/or the identifying of the one or more association variables are implemented in hardware, for example, using one or more application-specific integrated circuits (ASICs), and/or using software.

Figure 8A:
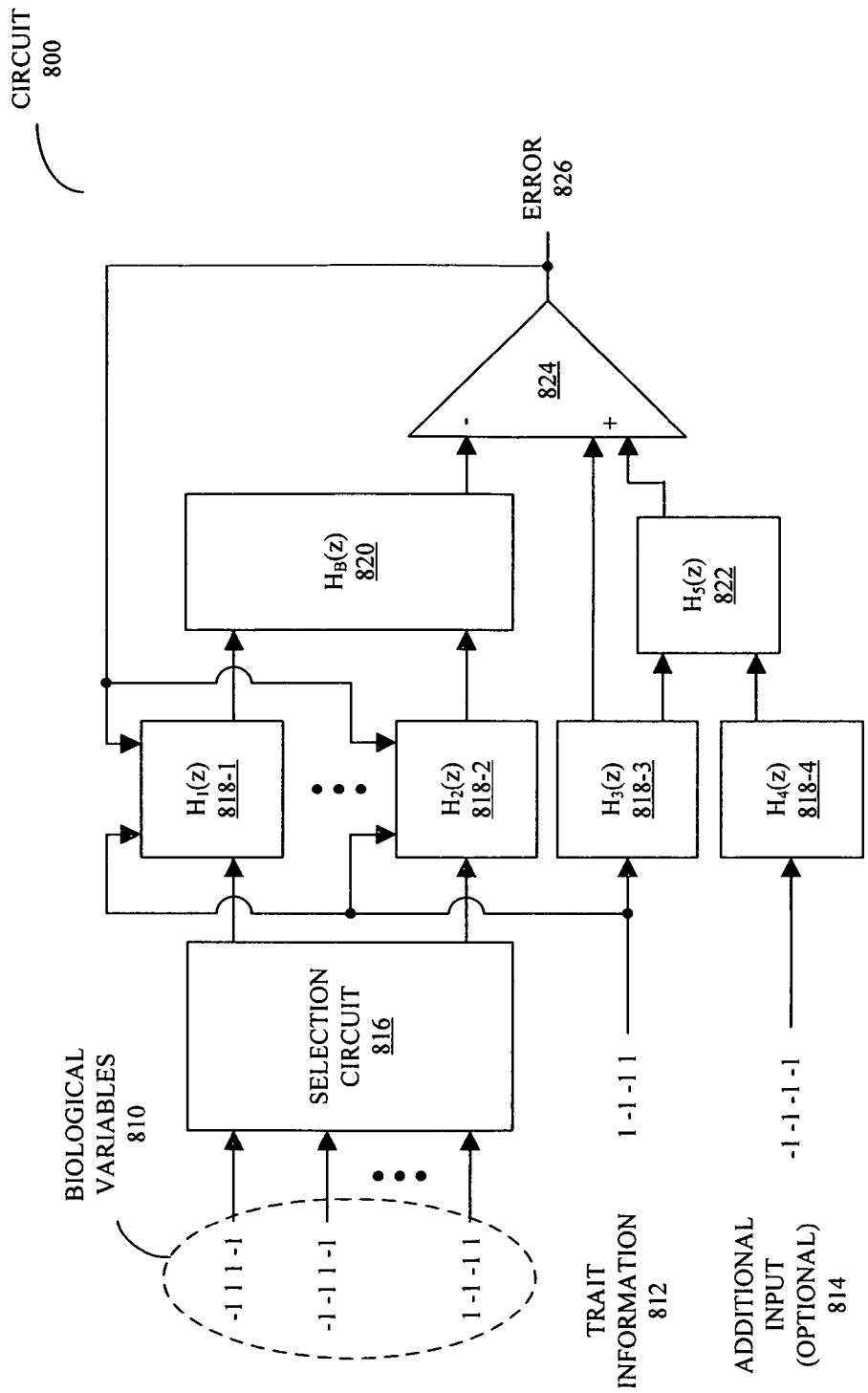
FIG. 8A is a block diagram illustrating a circuit in accordance with an embodiment of the present invention.

FIG. 8A presents a block diagram illustrating a circuit 800 for determining one or more statistical relationships and/or identifying one or more association variables. Presence (coded with 1s) and absence information (coded with −1 s) for one or more biological variables 810 are selectively coupled using selection circuit 816 to one or more filters H, 818. Note that the selection circuit 816 may be a multiplexer. In some embodiments, filters $H_i$ 818 perform spectral modification, such as limiting or excluding one or more of the biological variables 810. Moreover, filters $H_i$ 818 may convert the presence and absence information for one or more of the biological variables 810 into one or more patterns of occurrence.

Note that filters $H_i$ 818 may be adaptive. This adaptation may be based on trait information 812 and/or an error 826. In some embodiments, the adaptation includes one or more time intervals and/or one or more offsets between these time intervals, which are used when determining compound variables. Note that the adaptation may minimize or reduce the error 826 or a portion of the error 826.

Outputs from one or more of the filters $H_i$ 818 may be coupled to filter $H_B$ 820. This filter may perform additional spectral modification. As a consequence, an arbitrary filtering operation may be implemented using one or more of the filters $H_i$ 818 and/or the filter $H_B$ 820. Moreover, filter $H_B$ 820 may determine a pattern of occurrence for one or more biological variables 810 and/or one or more compound variables.

Trait information 812 may be filtered using filter $H_3$ 818-3. Comparisons between an output of filter $H_3$ 818-3 and an output of the filter $H_B$ 820 may be performed using statistical analysis element 824. In some embodiments, the statistical analysis element 824 may be a comparator. Statistical analysis element may implement one or more statistical analysis techniques, such as the log-likelihood ratio. Moreover, the statistical analysis element 824 may generate the error 826. Note that the error 826 may be: a scalar, a vector, and/or a matrix. In some embodiments, the statistical analysis element 824 may perform a relative time shifting of the output of filter $H_3$ 818-3 and the output of the filter $H_B$ 820.

In an exemplary embodiment, the statistical analysis element 824 calculates one or more statistical relationships between the trait information 812 and one or more patterns of occurrence of one or more compound variables. The one or more statistical relationships may be determined sequentially and/or substantially concurrently. Note that the error 826 may correspond to the one or more statistical relationships.

In some embodiments, one or more optional additional inputs, such as optional additional input 814, is filtered using one or more filters, such as filter $H_4$ 818-4, and/or combined with the trait information 812 using a filter, such as filter/combiner $H_5$ 822. An output from the filter/combiner $H_5$ 822 may be included in the analysis performed by the statistical analysis element 824. The one or more optional additional inputs may allow inclusion of cross-terms. In some embodiments, the one or more optional additional inputs may include other disease symptoms, other diseases (such as diseases that have a comorbidity with a trait), and/or environmental factors.

While a single output is shown for the filter $H_B$ 820, there may be additional outputs that are used by the statistical analysis element 824. Similarly, there may be additional outputs from the filter/combiner $H_5$ 822 that are used by the statistical analysis element 824.

While embodiment 800 uses presence and absence information in the one or more biological variables 810, the trait information 812, and the optional additional input 814, in some embodiments one or more of these items may only use presence information or may use only absence information. Alternatively or additionally, expression and/or suppression information may be used.

Figure 8B:
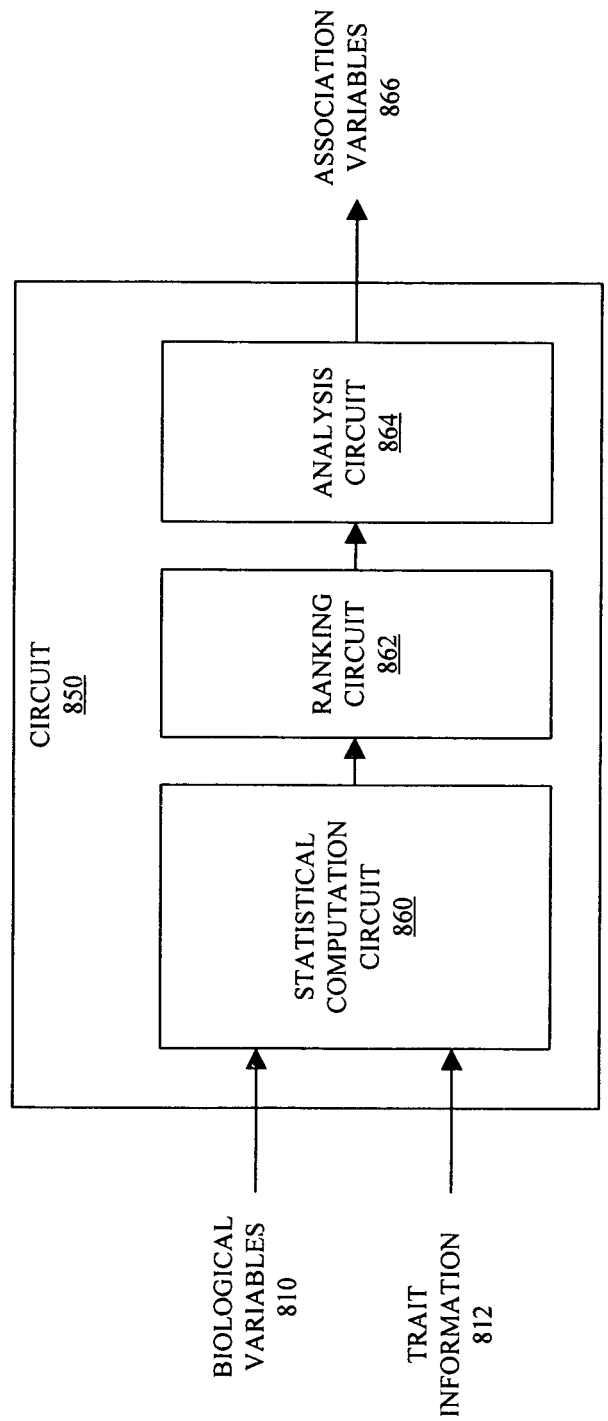
FIG. 8B is a block diagram illustrating a circuit in accordance with an embodiment of the present invention.

A more general description of a circuit to identify the one or more association variables is shown in FIG. 8B, which presents a block diagram illustrating circuit 850. In this circuit, biological variables 810 and trait information 812 are received by statistical computation circuit 860, which calculates the statistical relationships. (In some embodiments, one or more optional additional inputs, such as optional additional input 814 in FIG. 8A, are also received and used in the analysis.) Then, ranking circuit 862 determines the ranking of the number of occurrences of the biological variables 810 in the subset of the compound variables, and analysis circuit 864 identifies the one or more association variables 866 based on the ranking (such as the portion 718 in FIG. 7 which is substantially or approximately stable).

Circuits 800 (FIG. 8A) and 850 may include fewer components or additional components. Moreover, two or more components may be combined into a single component and/or a position of one or more components may be changed. In some embodiments the functionality of circuits 800 (FIG. 8A) and 850 is implemented more in hardware and less in software, or less in hardware and more in software, as is known in the art.

Devices and circuits described herein may be implemented using computer-aided design tools available in the art, and embodied by computer-readable files containing software descriptions of such circuits. These software descriptions may be: behavioral, register transfer, logic component, transistor and/or layout geometry-level descriptions. Moreover, the software descriptions may be stored on storage media or communicated by carrier waves.

Data formats in which such descriptions may be implemented include, but are not limited to: formats supporting behavioral languages like C, formats supporting register transfer level (RTL) languages like Verilog and VHDL, formats supporting geometry description languages (such as GDSII, GDSIII, GDSIV, CIF, and MEBES), and other suitable formats and languages. Moreover, data transfers of such files on machine-readable media may be done electronically over the diverse media on the Internet or, for example, via email. Note that physical files may be implemented on machine-readable media such as: 4 mm magnetic tape, 8 mm magnetic tape, 3½ inch floppy media, CDs, DVDs, and so on.

Figure 9:
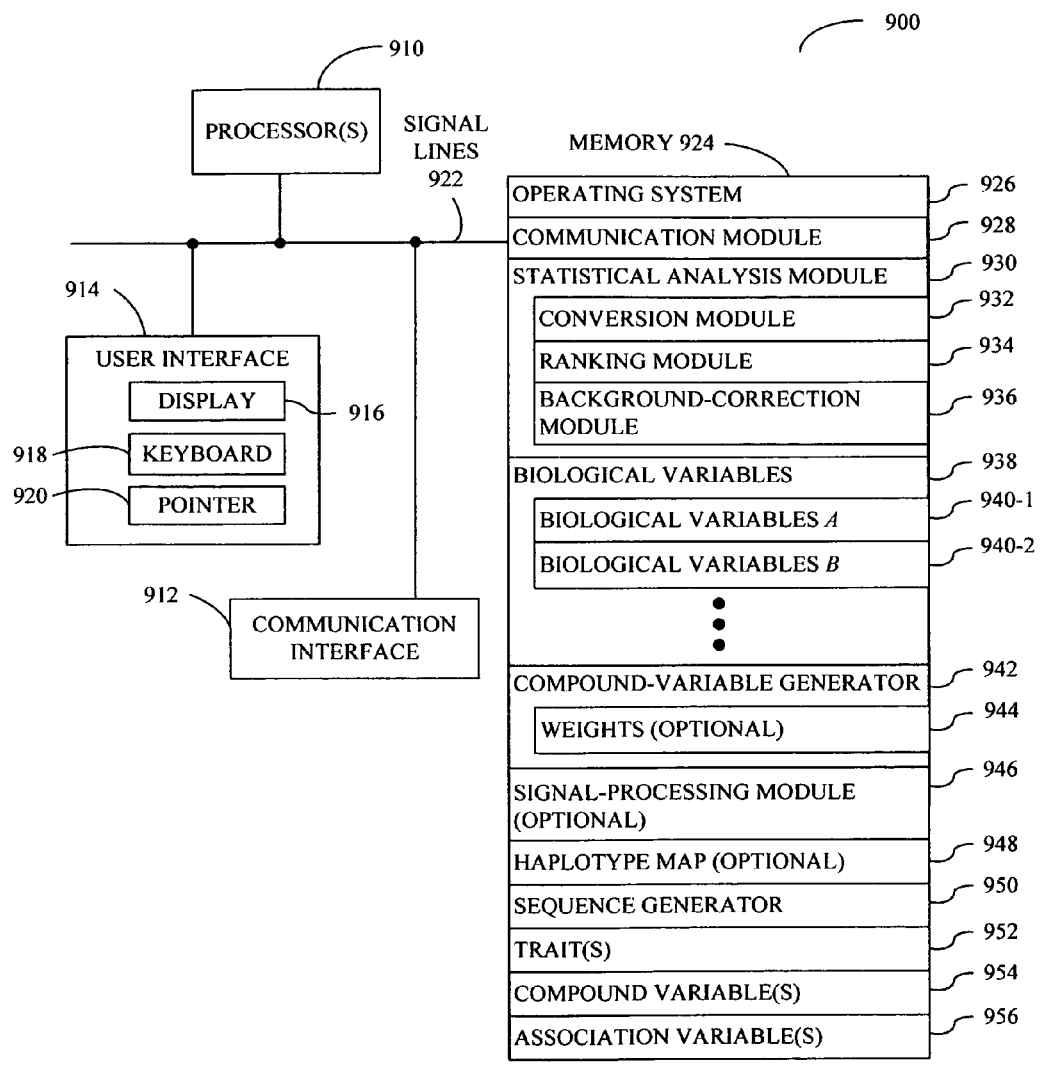
FIG. 9 is a block diagram illustrating a computer system in accordance with an embodiment of the present invention.

FIG. 9 presents a block diagram illustrating a computer system 900. Computer system 900 includes: one or more processors (or processor cores) 910, a communication interface 912, a user interface 914, and one or more signal lines 922 coupling these components together. Note that the one or more processors (or processor cores) 910 may support parallel processing and/or multi-threaded operation, the communication interface 912 may have a persistent communication connection, and the one or more signal lines 922 may constitute a communication bus. Moreover, the user interface 914 may include: a display 916, a keyboard 918, and/or a pointer 920, such as a mouse.

Memory 924 in the computer system 900 may include volatile memory and/or non-volatile memory. More specifically, memory 924 may include: ROM, RAM, EPROM, EEPROM, flash, one or more smart cards, one or more magnetic disc storage devices, and/or one or more optical storage devices. Memory 924 may store an operating system 926 that includes procedures (or a set of instructions) for handling various basic system services for performing hardware-dependent tasks. Moreover, memory 924 may also store communication procedures (or a set of instructions) in a communication module 928. These communication procedures may be used for communicating with one or more computers, devices and/or servers, including computers, devices and/or servers that are remotely located with respect to the computer system 900.

Memory 924 may also include one or more program modules 930, including: statistical analysis module 930 (or a set of instructions), conversion module 932 (or a set of instructions), ranking module 934 (or a set of instructions), background-correction module 936 (or a set of instructions), compound-variable generator 942 (or a set of instructions), optional signal-processing module 946 (or a set of instructions), and/or sequence generator 950 (or a set of instructions). Conversion module 932 may convert biological variables 938 for a group of life forms, such as biological variable A 940-1 or biological variable B 940-2, into categorical data. In some embodiments, biological variables 938 and/or information for one or more traits 952 associated with the group of life forms are preconditioned using optional signal-processing module 946. For example, optional signal-processing module 946 may filter data and/or may perform a transform, such as: a fast Fourier transform, a Laplace transform, a discrete Fourier transform, a Z-transform, and/or any other transform technique now known or later developed.

Then, compound-variable generator 942 may determine one or more compound variables 954 using at least some of the biological variables 938 (for example, statistical analysis module 930 may exclude one or more of the biological variables 938 using optional haplotype map 948). Alternatively, the compound variables 954 may be pre-determined. Note that in some embodiments the compound variables 954 are determined using optional weights 944.

Next, statistical analysis module 930 may determine statistical relationships between a pattern of occurrence of one or more traits 952 and patterns of occurrence of at least some of the compound variables 954. (Note that statistical analysis module 930 may exclude one or more of the compound variables 954 prior to determining the statistical relationships.) Moreover, ranking module 934 may determine one or more rankings of the number of occurrences of biological variables in statistically significant statistical compound variables above a noise floor.

Additionally, background-correction module 936 may determine another ranking based on statistical relationships between at least some of the compound variables 954 and a sequence of values generated using sequence generator 950. This other ranking may be subtracted from the ranking.

Then, statistical analysis module 930 may identify one or more association variables 956 based on the ranking (or the ranking after correcting for the background). In some embodiments, the operations of the various modules are repeated to higher order, i.e., in compound variables that include additional biological variables in the biological variables 938.

Instructions in the various modules in the memory 924 may be implemented in: a high-level procedural language, an object-oriented programming language, and/or in an assembly or machine language. The programming language may be compiled or interpreted, i.e., configurable or configured, to be executed by the one or more processors (or processor cores) 910.

Although the computer system 900 is illustrated as having a number of discrete components, FIG. 9 is intended to be a functional description of the various features that may be present in the computer system 900 rather than a structural schematic of the embodiments described herein. In practice, and as recognized by those of ordinary skill in the art, the functions of the computer system 900 may be distributed over a large number of servers or computers, with various groups of the servers or computers performing particular subsets of the functions. In some embodiments, some or all of the functionality of the computer system 900 may be implemented in one or more ASICs and/or one or more DSPs.

Computer system 900 may include fewer components or additional components. Moreover, two or more components may be combined into a single component and/or a position of one or more components may be changed. In some embodiments the functionality of computer system 900 may be implemented more in hardware and less in software, or less in hardware and more in software, as is known in the art.

Figure 10:
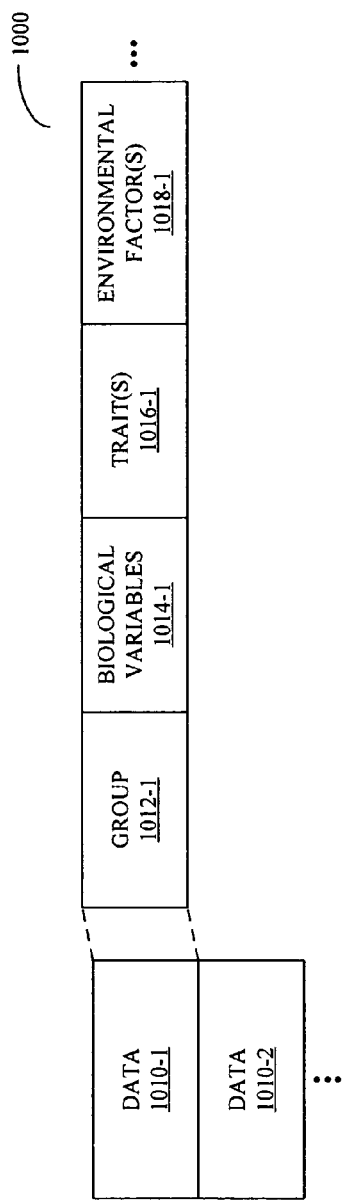
FIG. 10 is a block diagram illustrating a data structure in accordance with an embodiment of the present invention.

We now describe embodiments of a data structure that may be used in computer system 900. FIG. 10 presents a block diagram illustrating a data structure 1000. This data structure may include information or data 1010, such as biological variables, compound variables, and/or trait information associated with life forms in a group of life forms. For example, for data 1010-1, the information may include: group 1012-1, one or more biological variables 1014-1 associated with members of the group 1012-1, information about one or more associated traits 1016-1 of the members of the group 1012-1, and/or one or more environmental factors 1018-1 (which may be included with the one or more biological variables 1014-1).

Figure 11:
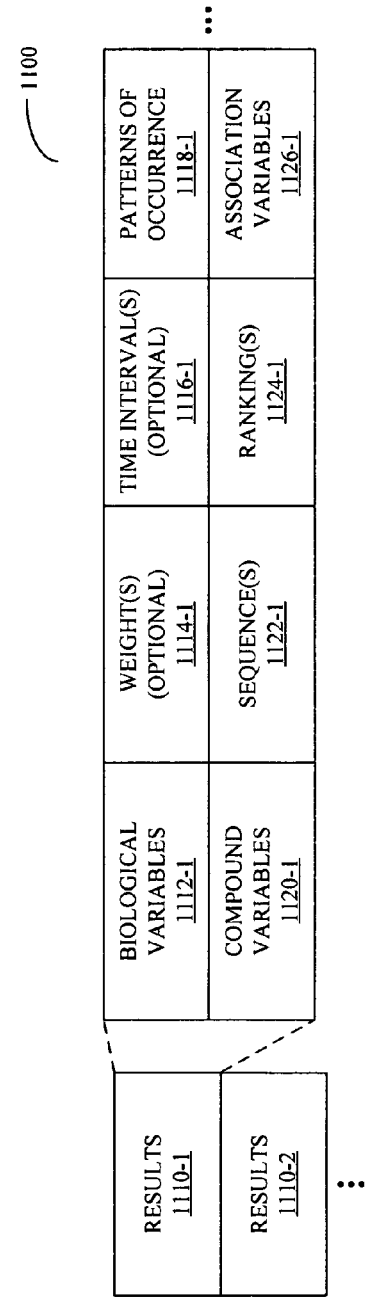
FIG. 11 is a block diagram illustrating a data structure in accordance with an embodiment of the present invention.

FIG. 11 presents a block diagram illustrating a data structure 1100. This data structure may include results 1110, such as statistical relationships, rankings, and/or association variables for one or more populations, such as the group of life forms, and/or one or more subsets of a given population. For example, results 1110-1 may include: one or more biological variables 1112-1, one or more optional weights 1114-1, one or more optional time intervals 1116-1, one or more patterns of occurrence 1118-1, one or more compound variables 1120-1, one or more sequences 1122-1 (such as a sequence of random or pseudorandom values), one or more rankings 1124-1, and/or one or more association variables 1126-1.

Note that in some embodiments of the data structures 1000 (FIG. 10) and/or 1100 there may be fewer or additional components. Moreover, two or more components may be combined into a single component and/or a position of one or more components may be changed.

While embodiments of apparatuses and related methods for identifying one or more association variables have been described, the apparatuses and related methods may be applied generally to determine statistical relationships in a wide variety of underdetermined problems in medicine, psychology, statistics, engineering, finance, applied mathematics and operations research. Consequently, the one or more association variables may be identified based on traits or features other than those corresponding to biological variables.

The foregoing descriptions of embodiments of the present invention have been presented for purposes of illustration and description only. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed:

1. An apparatus to identify one or more association variables that are associated with a phenotype, comprising:
    at least one processor;
    at least one memory; and
    at least one program module, the program module stored in the memory and configurable to be executed by the processor, the program module including:
        instructions for calculating statistical relationships between a pattern of occurrence in a group of life forms of the phenotype and patterns of occurrence in the group of life forms of pairwise combinations of biological variables in a set of biological variables of the group of life forms, wherein a given statistical relationship is between the pattern of occurrence in the group of life forms of the phenotype and a pattern of occurrence in the group of life forms of a given pairwise combination of biological variables,
        wherein the pattern of occurrence in the group of life forms of the given pairwise combination of biological variables is based on a pattern of occurrence in the group of life forms of a first biological variable in the set of biological variables, a pattern of occurrence in the group of life forms of a second biological variable in the set of biological variables, and a given mathematical operation,
        wherein the calculating includes contributions from presence and absence information in the pattern of occurrence in the group of life forms of the phenotype and presence and absence information in the patterns of occurrence in the group of life forms of the pairwise combinations of biological variables, and
        wherein, for each of the biological variables in the set of biological variables, the pairwise combinations of the biological variables in the set of biological variables include multiple instances of pairwise combinations;
        instructions for selecting a subset of the statistical relationships that exceed a statistical significance value;
        instructions for determining numbers of occurrences of the biological variables in the pairwise combinations of the biological variables corresponding to the statistical relationships in the subset, wherein the numbers of occurrences are other than patterns of occurrence in the group of life forms of individual biological variables in the set of biological variables and the patterns of occurrence in the group of life forms of the pairwise combinations of biological variables; and
        instructions for identifying one or more of the biological variables in the pairwise combinations of the biological variables as the one or more association variables based on the determined numbers of occurrences.

2. The apparatus of claim 1, wherein the given mathematical operation is other than linear superposition.

3. The apparatus of claim 1, wherein the given mathematical operation includes a logical operation.

4. The apparatus of claim 1, wherein the program module further includes instructions for ranking the biological variables based on the numbers of occurrences;

wherein an order of the biological variables in the ranking is approximately stable as a function of statistical significance values between the statistical significance value and another statistical significance, which is larger than the statistical significance value; and wherein the identifying is based on the ranking.

5. The apparatus of claim 1, wherein the statistical significance value corresponds to a noise floor in the statistical relationships.

6. The apparatus of claim 4, wherein the program module includes:

instructions for repeating the calculating, selecting, determining, and ranking operations using a generated sequence of values instead of the pattern of occurrence in the group of life forms of the phenotype; and instructions for subtracting, prior to the identifying, the ranking associated with the generated sequence of values from the ranking associated with the pattern of occurrence in the group of life forms of the phenotype.

7. The apparatus of claim 6, wherein the sequence of values include one of: a random and a pseudo-random sequence of values; and wherein a number of entries in the sequence of values equals a number of life forms in the group of life forms.

8. The apparatus of claim 6, wherein the statistical significance value used in the selecting operation associated with the sequence of values is different than the statistical significance value used in the selecting operation associated with the pattern of occurrence in the group of life forms of the phenotype.

9. The apparatus of claim 1, wherein the set of biological variables includes information associated with single nucleotide polymorphisms (SNPs); and wherein the program module includes instructions for converting the set of biological variables into categorical data based on minority allele frequencies of SNPs at genetic loci and majority allele frequencies of SNPs at genetic loci.

10. The apparatus of claim 9, wherein the presence information in the patterns of occurrence in the group of life forms of the pairwise combinations of biological variables includes expression or suppression of the biological variables; and wherein the absence information in the patterns of occurrence in the group of life forms of the pairwise combinations of biological variables includes absence of expression or absence of suppression of the biological variables.

11. The apparatus of claim 1, wherein the set of biological variables include one or more environmental factors.

12. The apparatus of claim 1, wherein the program module includes instructions for excluding at least some of the pairwise combinations of biological variables prior to calculating the statistical relationships; and wherein a given excluded pairwise combination of biological variables has a number of presences or absences in the pattern of occurrence in the group of life forms of the given excluded pairwise combinations of biological variables that is greater than a first value or less than a second value.

13. The apparatus of claim 1, wherein the program module includes instructions for determining the patterns of occurrence in the group of life forms of the pairwise combinations of biological variables.

14. The apparatus of claim 13, wherein the program module includes instructions for excluding at least some of the biological variables in the set of biological variables prior to determining the patterns of occurrence in the group of life forms of the pairwise combinations of biological variables; and wherein a given excluded biological variable has a number of presences or absences in a pattern of occurrence in the group of life forms of the given excluded biological variable that is greater than a third value or less than a fourth value.

15. The apparatus of claim 1, wherein the phenotype includes a trait in the group of life forms.

16. The apparatus of claim 1, wherein the phenotype includes a disease.

17. The apparatus of claim 1, wherein biological variables in the set of biological variables include epi-genetic information, information associated with deoxyribonucleic acid, information associated with ribonucleic acid, information associated with one or more proteins, or information associated with another biological marker.

18. The apparatus of claim 1, wherein a number of life forms in the group of life forms is significantly less than a number of biological variables in the set of biological variables so that the identifying operation constitutes an under-determined problem.

19. An electronic-device-implemented method for identifying one or more association variables that are associated with a phenotype, the method comprising:

calculating statistical relationships between a pattern of occurrence in a group of life forms of the phenotype and patterns of occurrence in the group of life forms of pairwise combinations of biological variables in a set of biological variables of the group of life forms, wherein a given statistical relationship is between the pattern of occurrence in the group of life forms of the phenotype and a pattern of occurrence in the group of life forms of a given pairwise combination of biological variables, wherein the pattern of occurrence in the group of life forms of the given pairwise combination of biological variables is based on a pattern of occurrence in the group of life forms of a first biological variable in the set of biological variables, a pattern of occurrence in the group of life forms of a second biological variable in the set of biological variables, and a given mathematical operation, wherein the calculating includes contributions from presence and absence information in the pattern of occurrence in the group of life forms of the phenotype and presence and absence information in the patterns of occurrence in the group of life forms of the pairwise combinations of biological variables and wherein, for each of the biological variables in the set of biological variables, the pairwise combinations of the biological variables in the set of biological variables include multiple instances of pairwise combinations;

selecting a subset of the statistical relationships that exceed a statistical significance value;

determining numbers of occurrences of the biological variables in the pairwise combinations of the biological variables corresponding to the statistical relationships in the subset, wherein the numbers of occurrences are other than patterns of occurrence in the group of life forms of individual biological variables in the set of biological variables and the patterns of occurrence in the group of life forms of the pairwise combinations of biological variables; and identifying one or more of the biological variables in the pairwise combinations of the biological variables as the one or more association variables based on the determined numbers of occurrences.

20. A computer-program product for use in conjunction with a computer system, the computer-program product comprising a non-transitory computer-readable storage medium and a computer program embedded therein for identifying one or more association variables that are associated with a phenotype, the computer program including:

instructions for calculating statistical relationships between a pattern of occurrence in a group of life forms of the phenotype and patterns of occurrence in the group of life forms of pairwise combinations of biological variables in a set of biological variables of the group of life forms, wherein a given statistical relationship is between the pattern of occurrence in the group of life forms of the phenotype and a pattern of occurrence in the group of life forms of a given pairwise combination of biological variables, wherein the pattern of occurrence in the group of life forms of the given pairwise combination of biological variables is based on a pattern of occurrence in the group of life forms of a first biological variable in the set of biological variables, a pattern of occurrence in the group of life forms of a second biological variable in the set of biological variables, and a given mathematical operation, wherein the calculating includes contributions from presence and absence information in the pattern of occurrence in the group of life forms of the phenotype and presence and absence information in the patterns of occurrence in the group of life forms of the pairwise combinations of biological variables and wherein, for each of the biological variables in the set of biological variables, the pairwise combinations of the biological variables in the set of biological variables include multiple instances of pairwise combinations;

instructions for selecting a subset of the statistical relationships that exceed a statistical significance value;

instructions for determining numbers of occurrences of the biological variables in the pairwise combinations of the biological variables corresponding to the statistical relationships in the subset, wherein the numbers of occurrences are other than patterns of occurrence in the group of life forms of individual biological variables in the set of biological variables and the patterns of occurrence in the group of life forms of the pairwise combinations of biological variables; and instructions for identifying one or more of the biological variables in the pairwise combinations of the biological variables as the one or more association variables based on the determined numbers of occurrences.

* * * * *